(12) United States Patent
So et al.

(10) Patent No.: US 11,925,488 B2
(45) Date of Patent: Mar. 12, 2024

(54) TOOLS AND INSTRUMENTS FOR USE WITH IMPLANTABLE ENCAPSULATION DEVICES

(71) Applicant: ViaCyte, Inc., San Diego, CA (US)

(72) Inventors: Vincent So, San Diego, CA (US); Erik Olson, San Diego, CA (US); Michael Scott, San Diego, CA (US); Chad Green, San Diego, CA (US); Giacomo Strollo, San Diego, CA (US); Gustavo Prado, San Diego, CA (US); Craig McGreevy, San Diego, CA (US); Laura Martinson, San Diego, CA (US); Donald Koenig, San Diego, CA (US)

(73) Assignee: ViaCyte, Inc., San Diego, CA (US)

( * ) Notice: Subject to any disclaimer, the term of this patent is extended or adjusted under 35 U.S.C. 154(b) by 0 days.

(21) Appl. No.: 17/367,203

(22) Filed: Jul. 2, 2021

(65) Prior Publication Data

US 2021/0330414 A1 Oct. 28, 2021

Related U.S. Application Data

(63) Continuation of application No. 14/254,844, filed on Apr. 16, 2014, now Pat. No. 11,051,900.

(51) Int. Cl.
*A61B 50/00* (2016.01)

(52) U.S. Cl.
CPC ...... *A61B 50/00* (2016.02); *A61B 2050/0067* (2016.02)

(58) Field of Classification Search
CPC ......... A61B 50/00; A61B 50/39; A61B 50/36; A61B 2050/314

(Continued)

(56) References Cited

U.S. PATENT DOCUMENTS

| 4,300,557 A | 11/1981 | Refojo et al. |
| 4,734,269 A * | 3/1988 | Clarke ................ A61M 1/3627 96/219 |

(Continued)

FOREIGN PATENT DOCUMENTS

| EP | 2332494 A1 | 6/2011 |
| JP | 2002-515783 A | 5/2002 |

(Continued)

OTHER PUBLICATIONS

International Search Report dated Jul. 14, 2014 which issued in connection with corresponding International Application No. PCT/US2014/034425 (5 pages total).

(Continued)

*Primary Examiner* — Anthony D Stashick
*Assistant Examiner* — Raven Collins
(74) *Attorney, Agent, or Firm* — Klarquist Sparkman, LLP

(57) ABSTRACT

Embodiments herein describe tools and instruments for holding, transferring, delivering, deploying an implantable device and methods and means of aseptically storing and shipping the implantable device including but not limited to a device case for protecting, housing and filling the device, a surgical sizer for preparing the implantable site, a deployer for transferring the implantable device from the device case and delivering or deploying the implantable device at the prepared implantable site.

13 Claims, 15 Drawing Sheets

(58) Field of Classification Search
USPC .......................................................... 206/438
See application file for complete search history.

(56) References Cited

U.S. PATENT DOCUMENTS

| | | | |
|---|---|---|---|
| 4,854,475 A | | 8/1989 | Riihimaki et al. |
| 5,011,472 A | | 4/1991 | Aebischer et al. |
| 5,125,920 A | | 6/1992 | Ishida |
| 5,284,481 A | | 2/1994 | Soika et al. |
| 5,295,964 A | * | 3/1994 | Gauthier ................ A61J 1/16 |
| | | | 604/113 |
| 5,314,471 A | * | 5/1994 | Brauker ................ A61F 2/022 |
| | | | 424/422 |
| 5,368,555 A | | 11/1994 | Sussman et al. |
| 5,545,223 A | | 8/1996 | Neuenfeldt et al. |
| 5,573,741 A | | 11/1996 | Riley |
| 5,593,440 A | | 1/1997 | Brauker et al. |
| 5,713,888 A | | 2/1998 | Neuenfeldt et al. |
| 5,733,336 A | | 3/1998 | Neuenfeldt et al. |
| 5,824,074 A | | 10/1998 | Koch |
| 5,964,261 A | | 10/1999 | Neuenfeldt et al. |
| 5,976,780 A | | 11/1999 | Shah |
| 6,060,640 A | | 5/2000 | Pauley et al. |
| 6,350,281 B1 | | 2/2002 | Rhee |
| 6,620,123 B1 | | 9/2003 | Mitragotri et al. |
| 6,814,086 B2 | | 11/2004 | Stallings |
| 6,887,239 B2 | | 5/2005 | Elstrom et al. |
| 7,078,760 B2 | * | 7/2006 | Coursey ................ G03F 7/091 |
| | | | 257/E21.026 |
| 7,427,415 B2 | | 9/2008 | Scharp et al. |
| 7,432,104 B2 | | 10/2008 | Mitalipova et al. |
| 7,510,876 B2 | | 3/2009 | D'Amour et al. |
| 7,534,608 B2 | | 5/2009 | Martinson et al. |
| 7,541,185 B2 | | 6/2009 | D'Amour et al. |
| 7,621,907 B2 | | 11/2009 | Rodstrom |
| 7,625,753 B2 | | 12/2009 | Kelly et al. |
| 7,695,963 B2 | | 4/2010 | Agulnick et al. |
| 7,695,965 B2 | | 4/2010 | Martinson et al. |
| 7,704,738 B2 | | 4/2010 | D'Amour et al. |
| 7,737,253 B2 | | 6/2010 | Robins et al. |
| 8,008,075 B2 | | 8/2011 | Green et al. |
| 8,129,182 B2 | | 3/2012 | D'Amour et al. |
| 8,153,429 B2 | | 4/2012 | Robins et al. |
| 8,211,699 B2 | | 7/2012 | Robins et al. |
| 8,216,836 B2 | | 7/2012 | D'Amour et al. |
| 8,338,170 B2 | | 12/2012 | Kelly et al. |
| 8,409,233 B1 | | 4/2013 | Chinn et al. |
| 8,480,969 B2 | | 7/2013 | Fukuzawa |
| 8,881,900 B2 | | 11/2014 | Witt et al. |
| 9,078,760 B2 | * | 7/2015 | Marshall ................ A61F 5/4408 |
| 9,101,465 B2 | | 8/2015 | Berner et al. |
| 10,092,507 B2 | * | 10/2018 | Hennemann ........... A61K 38/14 |
| 2002/0081724 A1 | | 6/2002 | Carpenter et al. |
| 2003/0198581 A1 | | 10/2003 | Sweet et al. |
| 2004/0072343 A1 | | 4/2004 | Verma et al. |
| 2005/0266554 A1 | | 12/2005 | D'Amour et al. |
| 2007/0122905 A1 | | 5/2007 | D'Amour et al. |
| 2008/0033544 A1 | | 2/2008 | Lemmon |
| 2009/0004238 A1 | | 1/2009 | Scharp et al. |
| 2009/0011502 A1 | | 1/2009 | D'Amour et al. |
| 2009/0042287 A1 | | 2/2009 | D'Amour et al. |
| 2009/0081296 A1 | | 3/2009 | Humes et al. |
| 2009/0104696 A1 | | 4/2009 | Robins et al. |
| 2009/0220959 A1 | | 9/2009 | D'Amour et al. |
| 2009/0253202 A1 | | 10/2009 | D'Amour et al. |
| 2009/0298178 A1 | | 12/2009 | D'Amour |
| 2010/0041150 A1 | | 2/2010 | Kelly et al. |
| 2010/0072216 A1 | | 3/2010 | Voute et al. |
| 2010/0124564 A1 | * | 5/2010 | Martinson ............... A61F 2/022 |
| | | | 424/424 |
| 2010/0151568 A1 | | 6/2010 | D'Amour et al. |
| 2010/0260728 A1 | | 10/2010 | Martinson et al. |
| 2010/0263545 A1 | | 10/2010 | Morgan et al. |
| 2010/0279399 A1 | | 11/2010 | Robins et al. |
| 2010/0298790 A1 | * | 11/2010 | Guidi ................... A61M 27/00 |
| | | | 604/319 |
| 2013/0115132 A1 | * | 5/2013 | Engimann .............. A61L 2/16 |
| | | | 206/363 |
| 2014/0014226 A1 | | 1/2014 | Green et al. |
| 2014/0286595 A1 | * | 9/2014 | Moreschini .............. A61L 2/26 |
| | | | 383/33 |
| 2014/0339114 A1 | | 11/2014 | Griffin |
| 2014/0339117 A1 | * | 11/2014 | Quan ................ A61B 50/3001 |
| | | | 206/438 |
| 2014/0346071 A1 | * | 11/2014 | Genosar ................ B65D 25/02 |
| | | | 206/438 |
| 2017/0072074 A1 | | 3/2017 | Gladnikoff et al. |

FOREIGN PATENT DOCUMENTS

| | | |
|---|---|---|
| JP | 2004-500158 A | 1/2004 |
| WO | 199802113 A1 | 1/1998 |
| WO | 0108630 A2 | 2/2001 |
| WO | 2005063971 A2 | 7/2005 |
| WO | 2008079997 A2 | 7/2008 |
| WO | 2010129294 A2 | 11/2010 |
| WO | 2010129294 A3 | 4/2011 |
| WO | 2012115619 A1 | 8/2012 |

OTHER PUBLICATIONS

Vertex Pharmaceuticals Incorporated, "Vertex to acquire ViaCyte, with the goal of accelerating its potentially curative VX-880 programs in Type 1 Diabetes," Press Release (Jul. 11, 2022).

* cited by examiner

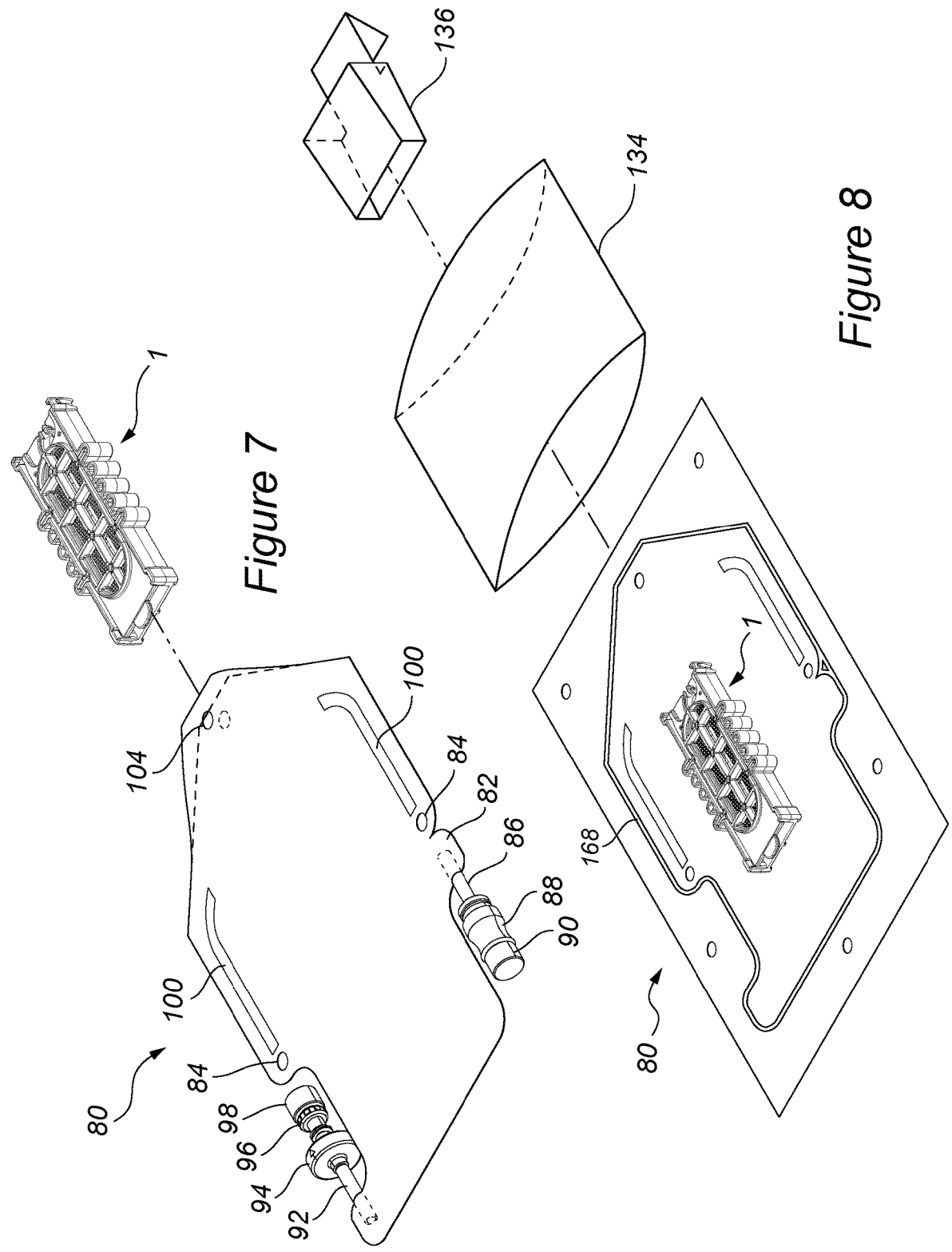

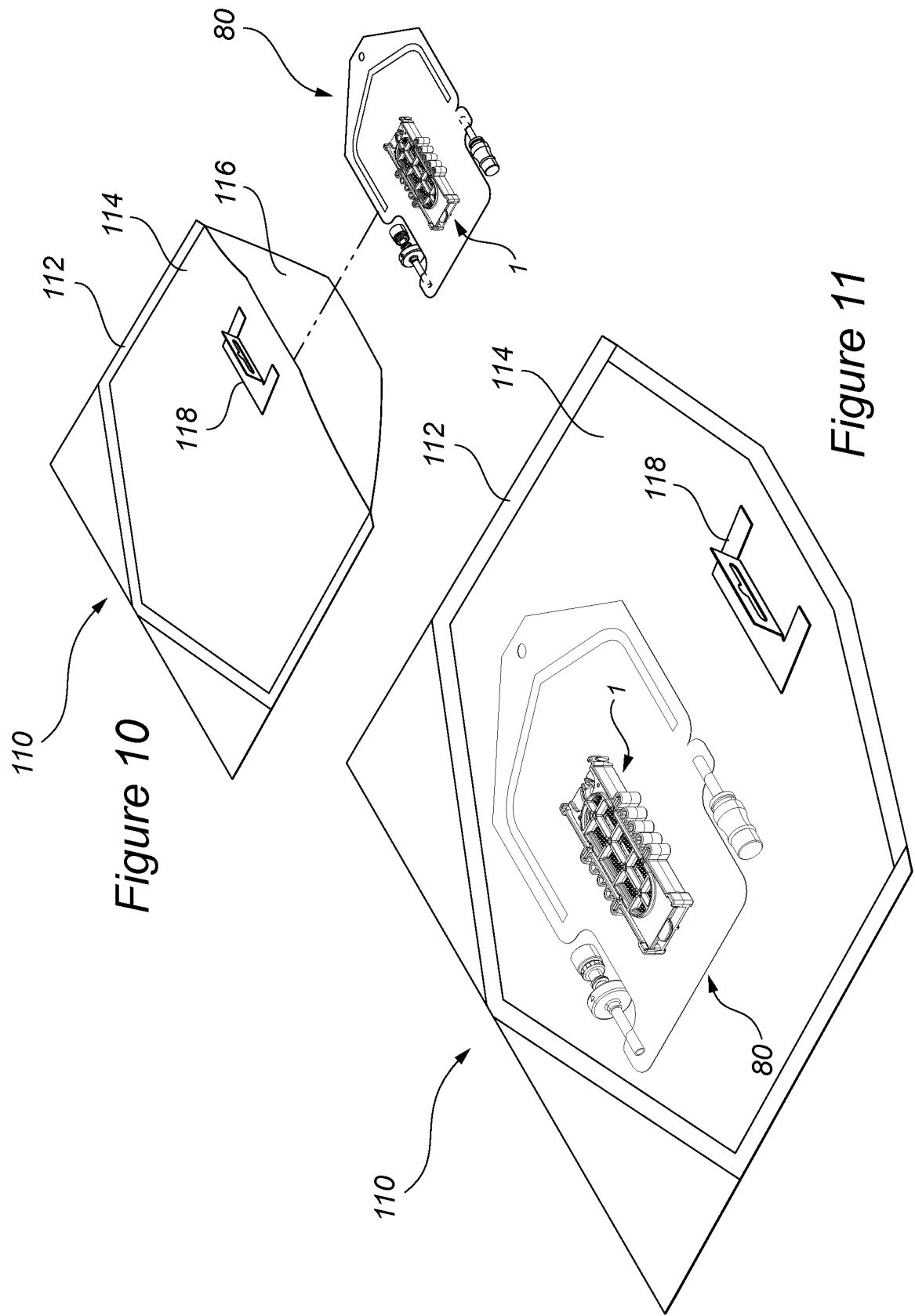

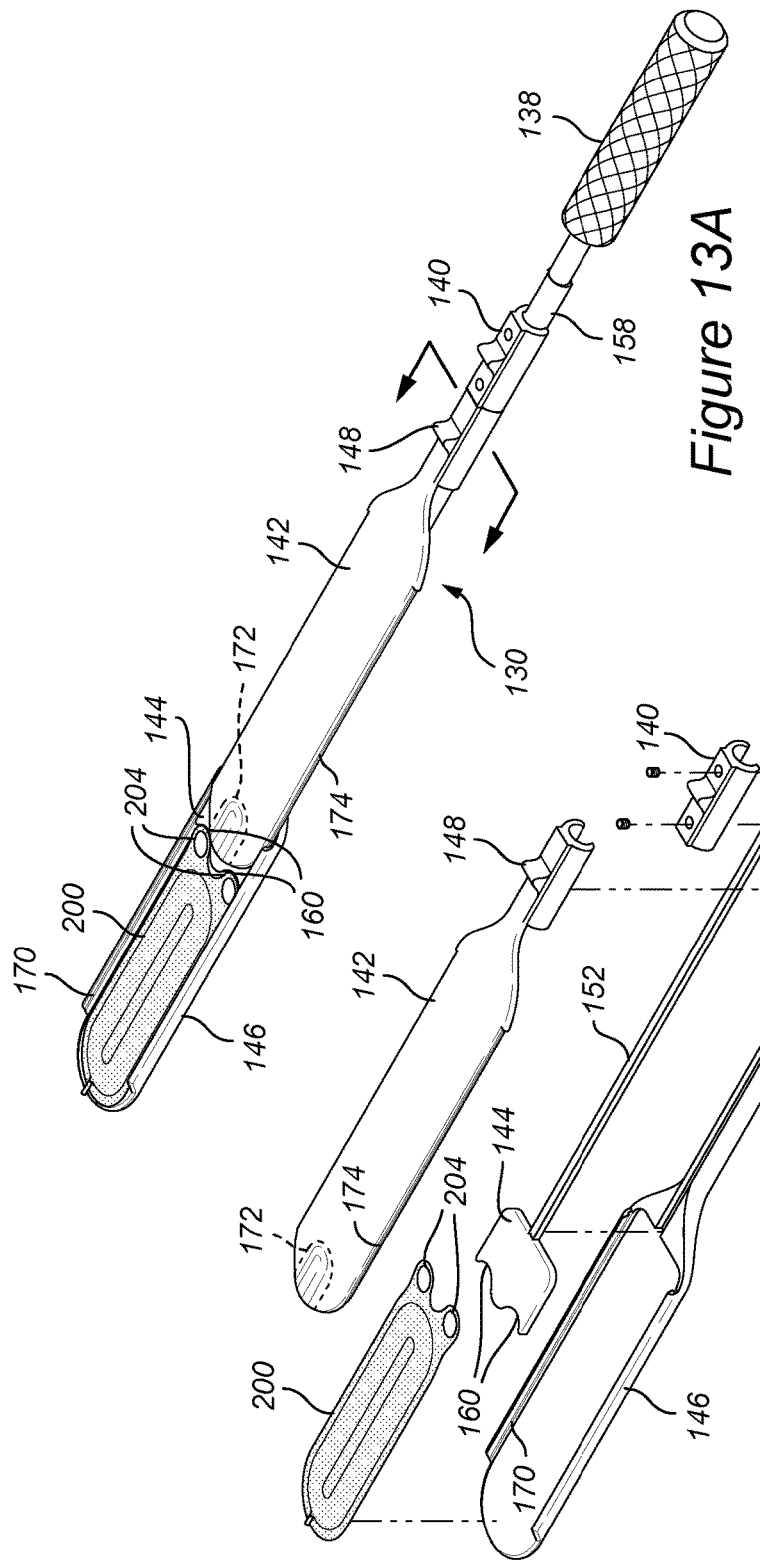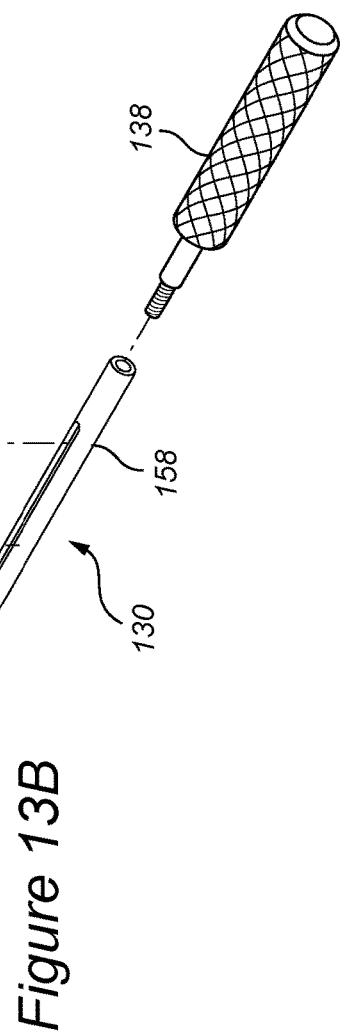
Figure 13A
Figure 13B

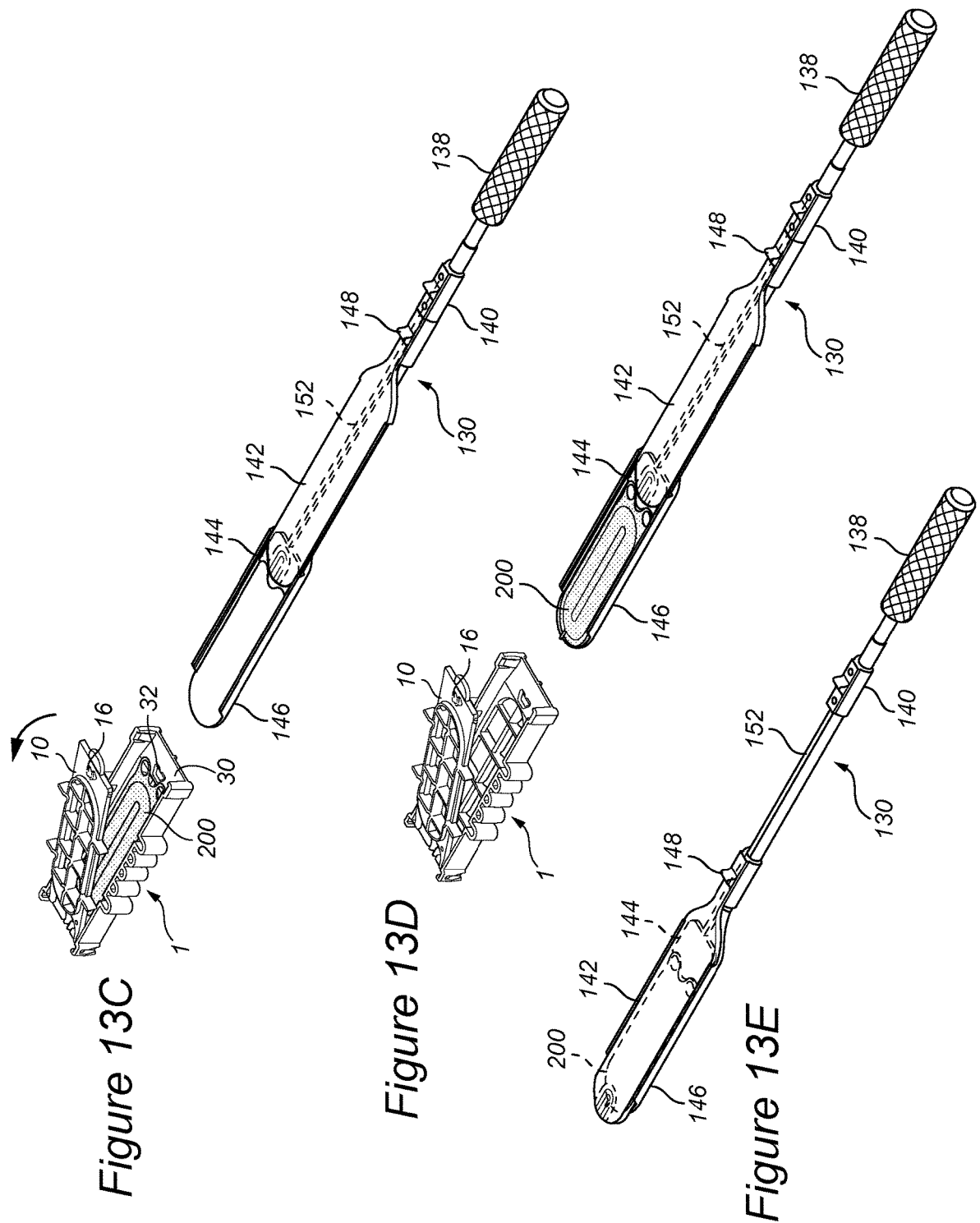

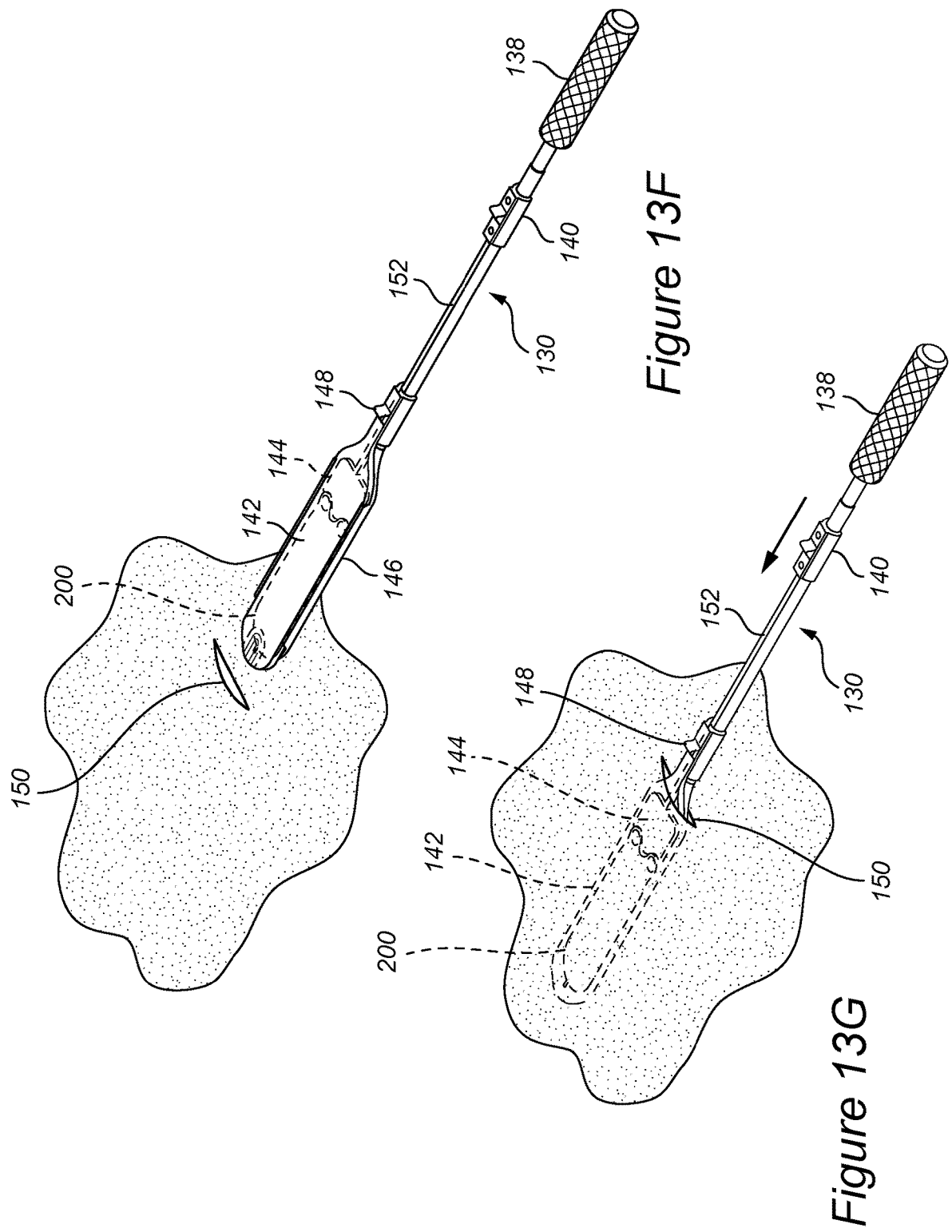

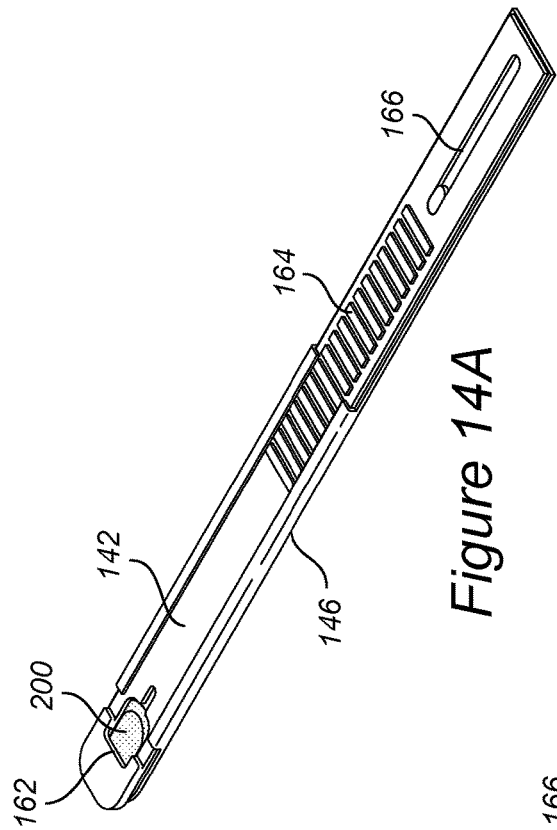
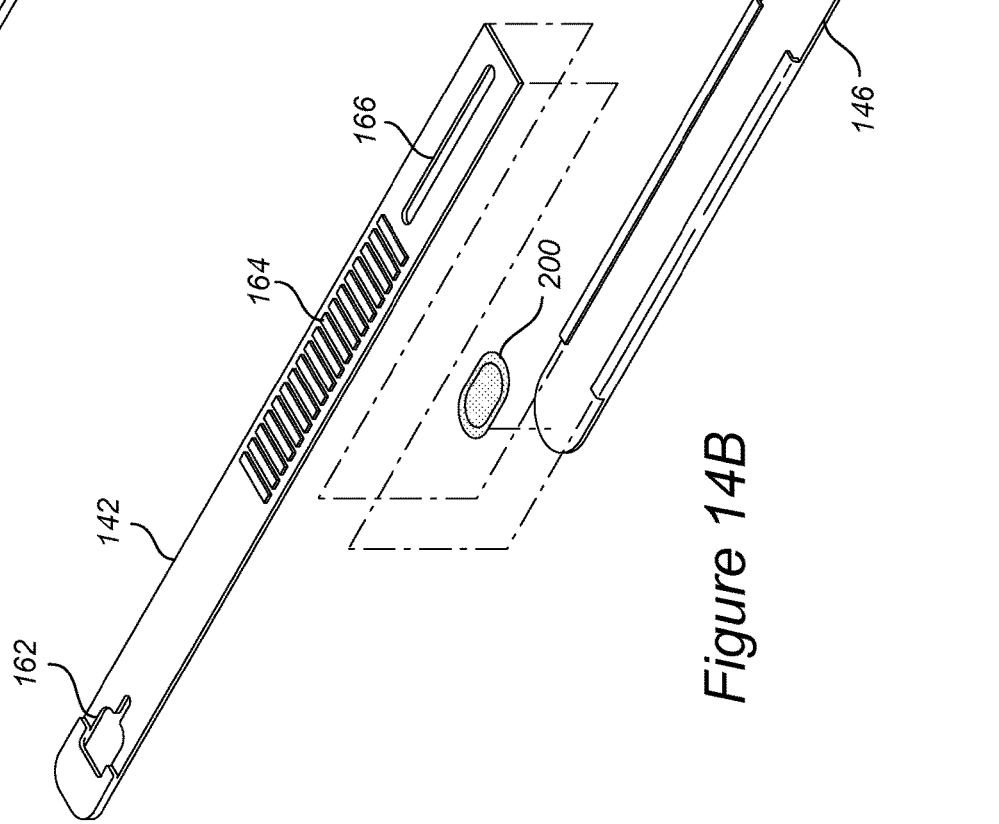

TOOLS AND INSTRUMENTS FOR USE WITH IMPLANTABLE ENCAPSULATION DEVICES

CROSS-REFERENCE TO RELATED APPLICATION

The present application is a continuation of U.S. application Ser. No. 14/254,844, filed Apr. 16, 2014, which is incorporated herein by reference.

STATEMENT OF GOVERNMENT SUPPORT

This research was made possible, in part, by an award from the California Institute for Regenerative Medicine (Award No. DR1-01423). The contents of this publication are solely the responsibility of the inventors and do not necessarily represent the official views of CIRM or any other agency of the state of California.

BACKGROUND OF THE INVENTION

1. Field of Invention

The present invention relates generally to a cellular therapy and means and methods for holding, transferring, sizing, marking and deploying a cell encapsulation implantable device for the treatment of human diseases, specifically, diabetes mellitus.

2. Description of Related Art

Cell replacement therapy for certain diseases can be therapeutically treated by transferring cells, tissues, or organs into a patient having the particular disease. The main hurdles to a commercial cell therapy remain a renewable cell source and an encapsulation source which provides alloprotection against host immunity. Ideally, such an implantable device minimizes or eliminates patient use of long term immune-suppressive drugs.

Previously, Applicants have described both a renewable cell source and macro-encapsulation drug delivery system suitable for at least the purpose of pancreatic progenitor cell delivery for production of insulin in vivo in response to glucose stimulation. See, for example, at least U.S. application Ser. No. 12/099,759, entitled METHODS OF PRODUCING PANCREATIC HORMONES, filed Apr. 8, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. No. 14/106,330, entitled IN VITRO DIFFERENTIATION OF PLURIPOTENT STEM CELLS TO PANCREATIC ENDODERM CELLS (PEC) AND IMMATURE BETA CELLS, filed Dec. 12, 2013; Ser. No. 14/201,630, filed Mar. 7, 2014; and PCT/US2014/026529, IN VITRO DIFFERENTIATION OF PLURIPOTENT STEM CELLS TO PANCREATIC ENDODERM CELLS (PEC) AND ENDOCRINE CELLS, filed Mar. 13, 2014; PCT/US2014/022109, 3-DIMENSIONAL LARGE CAPACITY CELL ENCAPSULATION DEVICE, filed Mar. 7, 2014; and U.S. Design application No. 29/408,366 filed Dec. 12, 2011; Ser. No. 29/408,368 filed Dec. 12, 2011; Ser. No. 29/423,365 filed May 31, 2012; Ser. No. 29/447,944 filed Mar. 13, 2013; Ser. Nos. 29/484,363, 29/484,359, 29/484,360, 29/484,357; 29/484,356, 29/484,355, 29/484,362 and 29/484,35, titled 3-DIMENSIONAL LARGE CAPACITY CELL ENCAPSULATION DEVICE and filed Mar. 7, 2014.

Such an encapsulated cell product ("combination product") for treatment of diabetes is not commercially available. A commercial combination product should provide systems and methods for securing and maintaining the integrity of an implantable device in its own case, an assembly for sterilizing the implantable device and case, filling the implantable device with living cells in an aseptic manner, storing and shipping the combination product to a clinical site, preparing an anatomical implantation site by sizing it and marking the anatomical implantation site, then holding, transferring and deploying the combination product to the anatomical implantation site.

SUMMARY OF THE INVENTION

Disclosed herein is a case for holding an implantable planar-shape device, the case comprising: a detachably connected cover body and base body, wherein the cover body has a first latch portion and the base body has a second latch portion configured to secure the cover body to the base body when the case is in a closed position, and wherein the cover body and the base body when secured comprise a volume having at least one opening to allow passage of one or more biologically active materials therethrough. Additional embodiments are disclosed.

The foregoing, and other features and advantages of the invention will be apparent from the following, more particular description of the preferred embodiments of the invention, the accompanying drawings, and the claims.

BRIEF DESCRIPTION OF THE DRAWINGS

For a more complete understanding of the embodiments of the invention, and the advantages thereof, reference is now made to the ensuing descriptions taken in connection with the accompanying drawings briefly described as follows:

FIG. 7 illustrates a perspective view of a device case storage container according to an embodiment of the invention;

FIG. 8 illustrates an exploded perspective view of the FIG. 7 device case storage container and components for inserting the device case and implantable device therein, with the cover sheet of the container removed for clarity of illustration, according to an embodiment of the invention;

FIG. 10 illustrates a perspective view of a device case storage container shipping bag, with the cover sheet of the container removed for clarity of illustration, according to an embodiment of the invention;

FIG. 11 illustrates a perspective view of a device case storage container shipping bag with a device case storage container therein, with the cover sheet of the container removed for clarity of illustration, according an embodiment of the invention;

FIGS. 13A-13I illustrate exploded perspective views of, and sequences of using, an implantable device deployer (FIG. 13A), a implantable device deployer to show the component parts (FIG. 13B), during transfer of the implantable device from the device case (FIG. 13C-E), delivery and deployment of the implantable device at the implant site (FIG. 13F-H), and a cross-section of the shaft of the deployer (FIG. 13I) according an embodiment of the invention; and FIGS. 14A-14C illustrate perspective views of an alternative implantable device deployer embodiment (FIG. 14A), an exploded perspective view of the implantable device deployer to show the component parts thereof (FIG. 14B), and after delivery and deployment of the implantable device at the anatomical implant site (FIG. 14C) according an embodiment of the invention.

DETAILED DESCRIPTION OF EMBODIMENTS

Figure 1:
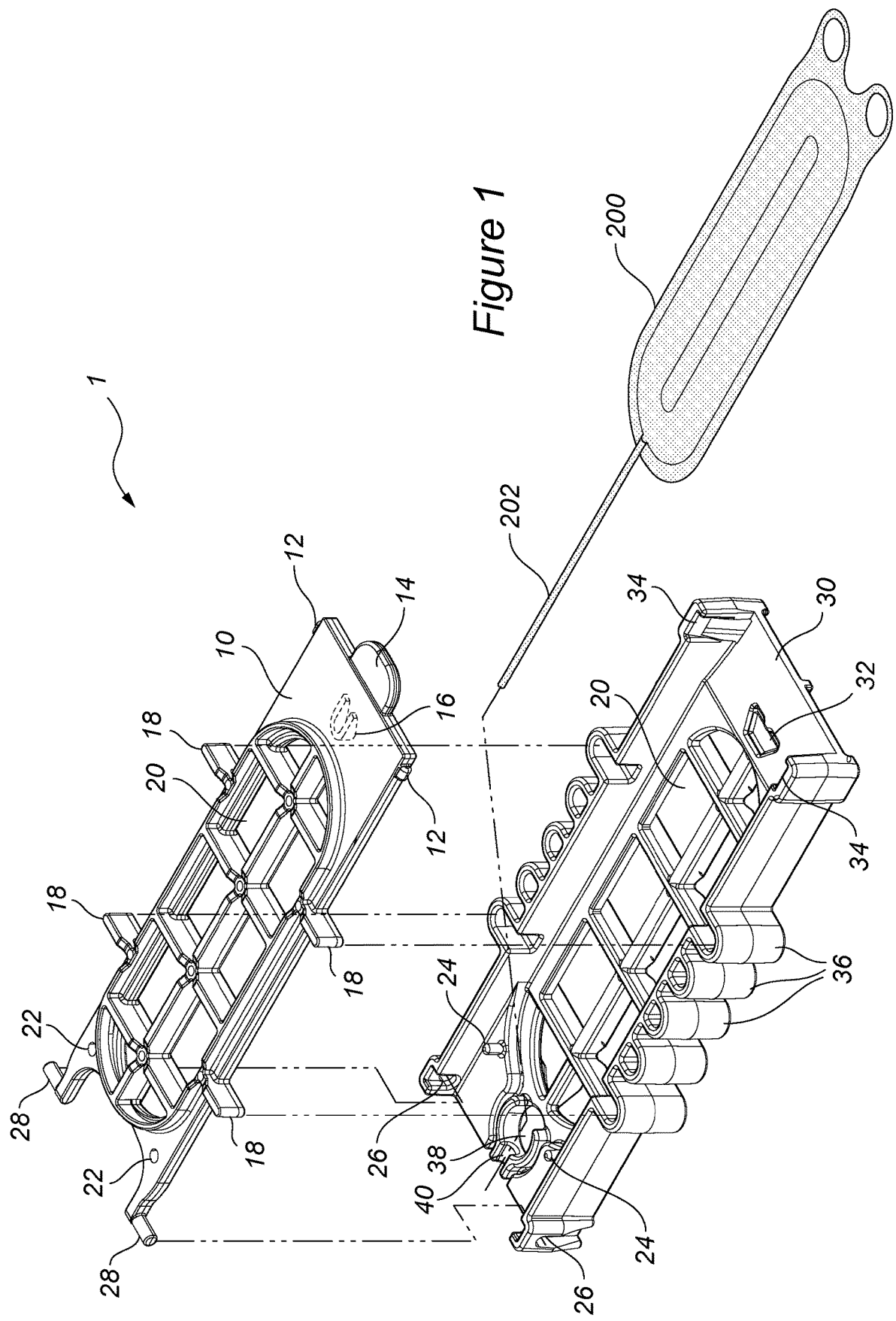
FIG. 1 illustrates an exploded perspective view of a device case to show the component parts and an implantable device according to an embodiment of the invention.

Further features and advantages of the invention, as well as the structure and operation of various embodiments of the invention, are described in detail below with reference to the accompanying FIGS. 1-14, wherein like reference numerals refer to like elements. Although embodiments of the invention are described in the context of implantable devices with pancreatic progenitor cells for the treatment of diabetes mellitus, one of ordinary skill in the art readily appreciates that the present invention is applicable for macro-encapsulation of any type of living cells, therapeutic agents, or mixtures thereof, including but not limited to thyroid cells, parathyroid cells, pancreatic cells, intestinal cells, thymus cells, hepatic cells, endocrine cells, skin cells, hematopoietic cells, bone marrow stem cells, renal cells, muscle cells, neural cells, stem cells, embryonic stem cells, lineage-restricted cells, progenitor cells, precursor cells, genetically engineered cells, tumor cells, and derivatives and combinations thereof for the treatment of one or more disease or disorder, including, but not limited to diabetes mellitus. Also contemplated are cells producing cell-based products such as proteins (e.g. hormones and/or other proteins deficient in human diseases and the like), antibodies, antibiotics, lymphokines and the like for therapeutic indications. One of ordinary skill in the art also appreciates that the present invention is applicable to different implantable device types, materials, sizes, and/or configurations.

Various publications including scientific journal articles, patent publications and patents are herein referred to and the disclosure of each of them is incorporated herein by reference in its entirety. For example, methods of making insulin-producing cells and the implantation of implantable devices with pancreatic progenitors derived from human pluripotent stem cells for the production of insulin-producing cells are disclosed in Applicants U.S. Pat. Nos. 7,534,608; 7,695,965; 7,993,920; 8,338,170; 8,278,106; and 8,425,928; and are incorporated herein by reference in their entirety.

Device Case

FIGS. 1-4 illustrate nonlimiting, nonexclusive embodiments of a case 1 to secure and maintain the integrity of an implantable device. The case is also referred to an "implantable device case", "device case", "cage", "case" or equivalents thereof. For example, in one embodiment the device case maintains the integrity of the implantable device when the implantable device is sterilized or sterilizable (e.g. autoclave-safe), transferred, filled and the like. The case is generally a case 1 that comprises a first portion (e.g., a lid, cover, cover body, top body) 10, a second portion (e.g., bottom, base, tray, base tray, receptacle body) 30, a third portion (e.g., windows, openings, partitions, sections) 20, a fourth portion (a grippable means e.g. finger grips, handle, side walls) 36, a fifth portion (e.g., a hinge system) 26, 28, a sixth portion (a lock, latch or closing or attachment system e.g. latch or snap enclosures) 16, 32, seventh portion (a port sealing area or port sealing stage area) 38, and an eight portion (e.g. a ramp and/or side rails to accommodate and guide the deployer). The case 1 is generally configured to house an implantable device 200 therein, but can be configured to house any device, instrument, component, apparatus, element, material and the like therein with the purpose of securing and maintain the integrity of such device, instrument, component, apparatus, element, material and the like.

Figure 2:
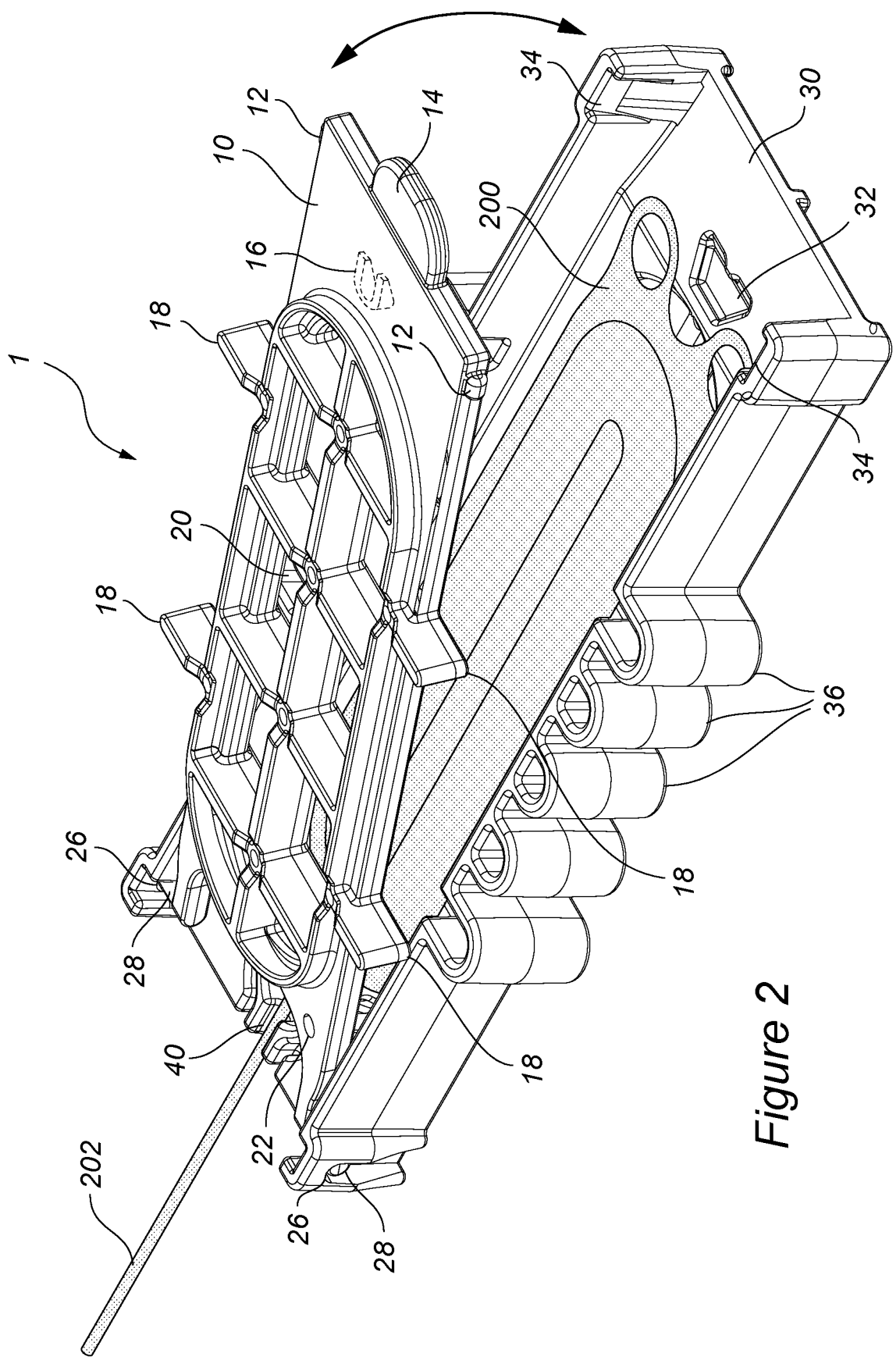
FIG. 2 illustrates a perspective view of an open device case of the invention as illustrated in FIG. 1 having a base body and cover body attachable at the hinge and containing an implantable device with a port therein.
Figure 3:
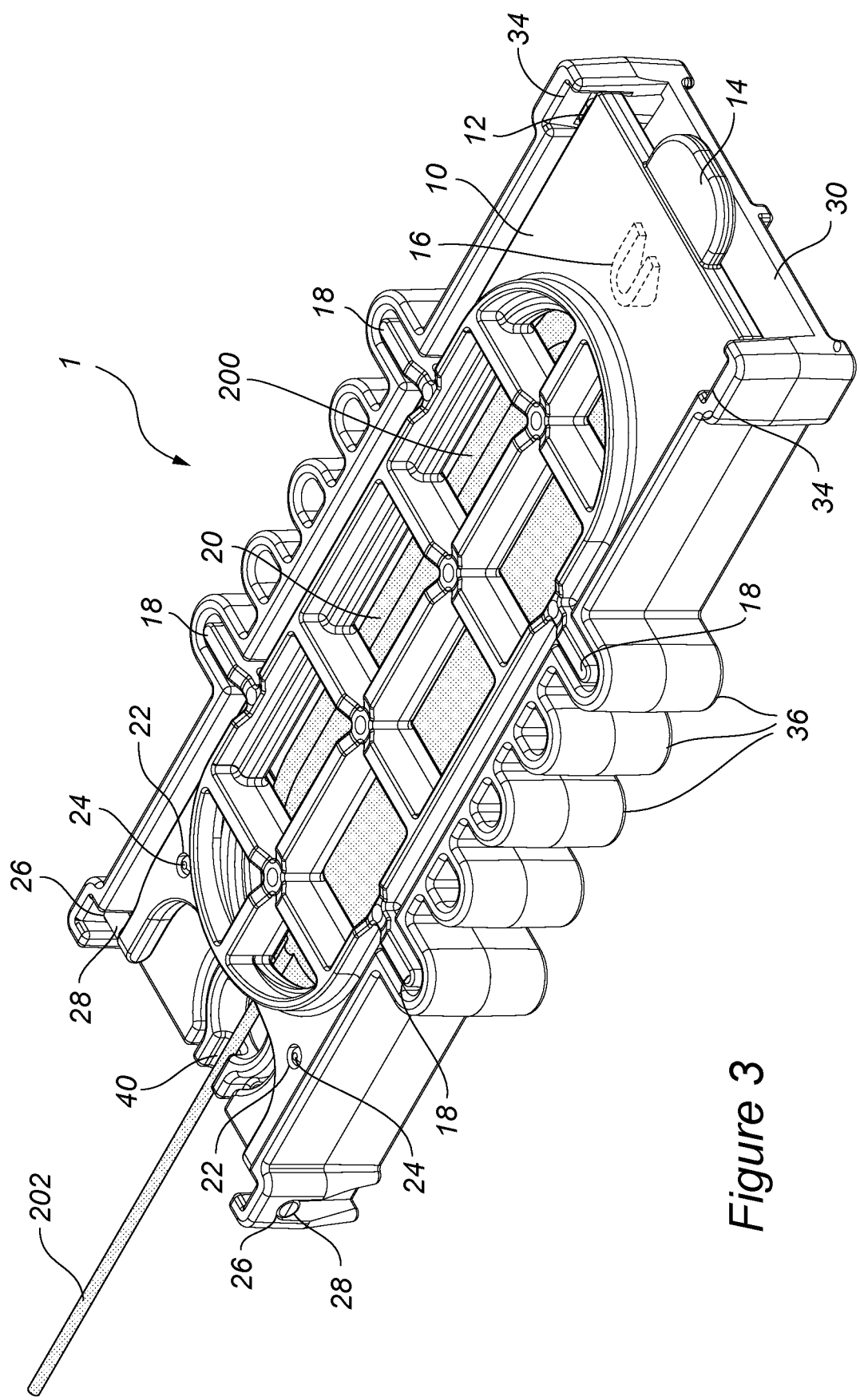
FIG. 3 illustrates a perspective view of a closed device case of the invention as illustrated in FIG. 1 with the base body and cover body attachable at the hinge and containing an implantable device with a port therein.
Figure 4A:
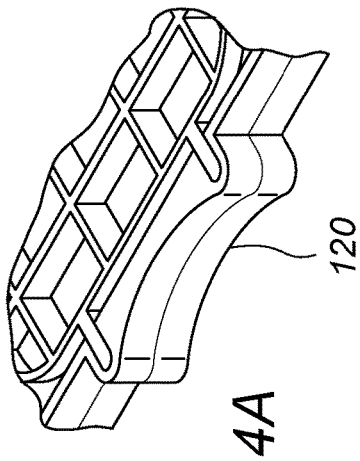
FIGS. 4A-4E illustrate a perspective views of finger grip configurations according to embodiments of the invention.
Figure 4B:
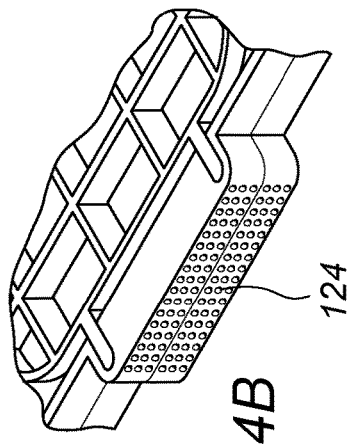
Figure 4C:
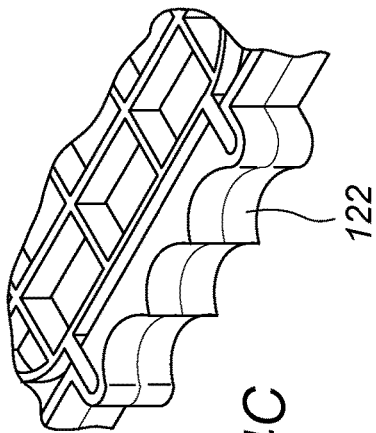
Figure 4D:
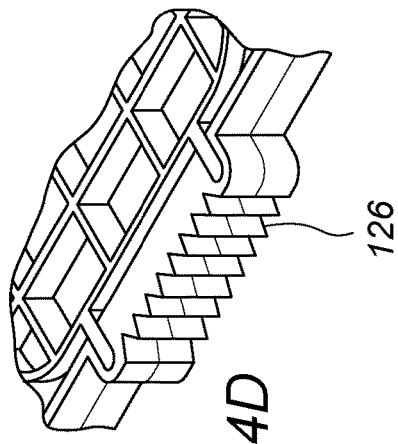
Figure 4E:
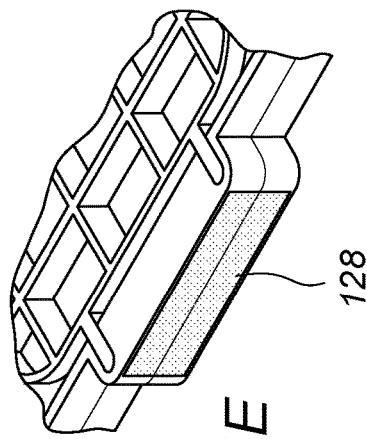

The case 1 may have any number of "coupling system,", "attachment system", "closing system" or equivalents thereof and refers to any system for closing, attaching, coupling or connecting one portion to another portion such as a hinge 26, 28, snap 16, 32, 12, 34 button, string, hook, latch and loop fasteners or other types of fasteners used to couple the cover body 10 to the base body 30 and define a volume to receive materials, such as an implantable device and/or biologically active materials. FIGS. 2-3 show the cover body 10 coupled to the base body 30 such that the cover body 10 moves between a first or closed position (FIG. 3), wherein the implantable device 200 provided therein is partly concealed, and a second or open position (FIG. 2), wherein the implantable device 200 provided therein is revealed or exposed. As illustrated, the cover body 10 and base body 30 can be coupled by one or more, such as two, coupling system to secure the cover body 10 and base body 30 together in a manner which allows the cover body 10 and base body 30 to move independently of the other. One such coupling system is illustrated in FIG. 1, for example, a hinge mechanism 26, 28, that pivotally couples the cover body 10 to the base body 30 relative to each other. The hinge mechanism 26, 28 generally comprises a pivot shaft or rod 28 inserted into an aperture or bore 26. As illustrated the rod 28 is attached to the distal end of the cover body 10, but it can also be attached to the base body 30. The pivot rod 28 may be integrally formed with the cover body 10 or the base body 30, or it may be provided as a separated component. Another way to attach the cover body 10 and base body 30 to each other is a latching system 16, 32, 12, 34 as illustrated in FIG. 1. Such a system can be provided to lock the cover body 10 and the base body 30 at the most proximal end 16, 32, or on the side walls 12, 34. One purpose of the latching systems shown herein is to prevent the implantable device 200 from sliding out of the case 1 or from moving or traveling while housed in the case 1. As illustrated, a user would use a snap 14 to apply a deliberate force against a friction fit of the snap and open or uncouple the latching system 16, 32, 12, 34 before loading or retrieving the implantable device 200 inside the case 1. Although one side wall latching system 12, 34 is shown, other similar latching system can be incorporated throughout the long axis of the case accordingly and will depend, in part, on the shape and design of the implantable device, instrument, component, apparatus, element, material and the like encased therein.

In another aspect, the case consists of at least one registration hole 22 located generally on the cover body 10 and its complementary matching pin 24 on the base body 30, such that the pin 24 inserts into the registration hole 22 therein as shown in FIG. 1 and provides a feature for interacting or connecting with the implant tool, such as a deployer, an embodiment of the invention as described in more detail below. Another coupling system is any number of feet projections 18 on the cover body 10, which in FIGS. 1-4 are shown to fit inside the internal aspect of a side walls of the cover body and base body, or finger grip 36. For example, FIG. 1 depicts one embodiment whereby the feet projections 18 fit or connect or slot into one section of the finger grip 36. Such feet projections are useful for at least preventing movement or travel of the cover body 10 relative to the base body, prevent the collapse of the cover body onto the base body, and holds or secures the implantable device 200 therein.

Figure 5:
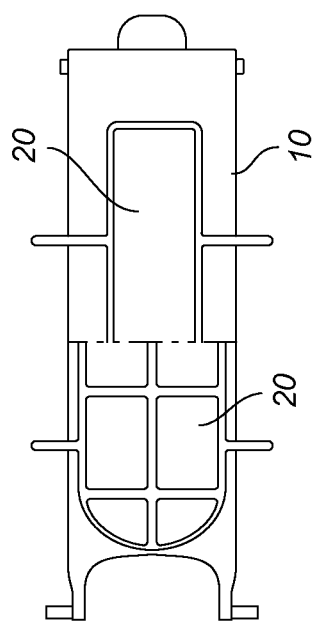
FIG. 5 illustrates a top view of window configurations on the cover body and base body of a device case according to an embodiment of the invention.

FIGS. 1-4 show the cover body 10 and base body 30 consisting of at least one opening or window 20. The windows 20 are configured to allow passage of the one or more biologically active materials between the interior and the exterior of the implantable device 200 therethrough. Although as illustrated the windows are of rectangular or semi-circle in shape, the windows 20 can be of any shape, design or number, which will in part depend on the shape and design of the device, instrument, component, apparatus, element, material and the like encased therein. FIGS. 1-4 show the window 20 configurations on the cover body 10 and the base body 30 as being symmetrical, but they need not be symmetrical so long as they allow movement of one or more biologically active materials into and out of the implantable device. Alternatively, FIG. 5 shows a window 20 configuration whereby the cover body 10 includes one large rectangular shape window 20, while the base body 30 includes more than one window 20 type. Still depending on the type and manner of device, instrument, component, apparatus, element, material and the like encased therein, the windows may further include a mesh or thin polymer, film or matrix, which certain of these polymers or films can allow for the visualization of the implantable device and provides similar permeability and passage of nutrient medium.

The implantable device 200 illustrated herein is a macro-encapsulation implantable device further consisting of welded semi-permeable polymer materials and at least one implantable device port 202 which is used to fill or load a therapeutic agent into the implantable device 200. However, modifications that do not depart from the device case embodiments described herein can be used to hold various implantable devices. And, in fact, Applicants have described various planar and non-planar (e.g. 3-dimensional) implantable devices that are contemplated including but not limited to self-expanding implantable devices, large capacity or macro-encapsulation, planar and non-planar implantable devices, or 3-dimensional macro-encapsulation implantable devices. Other encapsulation implantable devices have been described by Applicant, for example, PCT/US2014/022109, 3-DIMENSIONAL LARGE CAPACITY CELL ENCAPSULATION DEVICE, filed Mar. 7, 2014; and U.S. Design application No. 29/408,366 filed Dec. 12, 2011; Ser. No. 29/408,368 filed Dec. 12, 2011; Ser. No. 29/423,365 filed May 31, 2012; Ser. No. 29/447,944 filed Mar. 13, 2013; Ser. Nos. 29/484,363, 29/484,359, 29/484,360, 29/484,357; 29/484,356, 29/484,355, 29/484,362 and 29/484,35, titled 3-DIMENSIONAL LARGE CAPACITY CELL ENCAPSULATION DEVICE and filed Mar. 7, 2014.

FIGS. 1-3 show the case 1 having a port sealing stage area 38, which includes a cut-out or opening in the cover body 10 and base body 30 that allows for at least welding or any sealing instrument that is capable of welding and/or sealing an implantable device port 202 once the implantable device 200 is filled. The welding or sealing instrument can be hand held or mounted. Alternatively, the case 1 may also have a port guide 40 to align the port 202 in the port sealing stage area 38.

To maintain the integrity of the implantable device 200, the case 1 may generally also include side walls having rigid or not rigid grips, for example finger grips 36, which allow for easy handling and manipulation of the case 1 as shown in FIGS. 1-4. This is beneficial, e.g. during the device cell filling process and/or retrieval and transfer of the device, or manipulation by the handler. FIGS. 1-4 show five finger grips 36 on each side wall of the case 1, however, FIG. 5 shows other nonlimiting, nonexclusive finger grip configurations including indented fingers grips 120, 122, textured finger grips 124, 126, 128, engraved or etched finger grips 124, and rubberized or textured sticky finger grips 124, 128. Techniques and methods for making finger grips are well known in the art. Alternatively, should handling, assembling, filling, sealing the implantable device port, transferring, storing and shipping, and deploying the implantable device become automated; the finger grips can be optimized for such automation or not be incorporated, or incorporated elsewhere in the case.

In one embodiment, the implantable device 200 can undergo various quality controls testing while inside the case 1. Depending on the quality control testing, various one testing parameters will be used. For example, a dry or wet visual inspection using the naked eye and/or a microscope can determine the quality of the implantable device. In one embodiment, a dry visual inspection of the implantable device 200 can be performed first outside of the device case 1 followed by inside the case 1 using microscopy. In one embodiment, a wet visual inspection can also be performed by submerging the implantable device in a petri dish filled with isopropyl alcohol (IPA) and the implantable device 200 is inflated for about 30, 40, 60, 80, or 100 seconds during which period visual inspection for both sides of the implantable device is performed. For both dry and wet visual inspections, the quality value index could be a breach (e.g. a tear, a perforation, a leak, or physical abnormalities that may lead to a potential breach and the like) of the device can be determined using the naked eye and/or a microscope.

In one embodiment, a pressure decay quality control testing can be performed on the implantable device 200 inside the case 1. Pressure decay is a non-destructive test which will be performed on all implantable devices. In one embodiment, pressure decay testing can be preceded by dry and wet visual inspection of the implantable devices. Various instruments can be used for pressure decay testing including but not limited to the USON leak testers such as the Raptor, Sprint iQ, Qualitek mR, Optima vT and Vector; and preferably the USON Sprint iQ. For the pressure decay test, the device case 1 with the implantable device 200 therein is again fully submerged in a wetting solution containing IPA. The device should preferably remain still or unmoved during this testing as potentially any movement can affect the measurement. Pressure decay is a measure of decay over time. Implantable devices 200 that pass the pressure decay test will have quality index measurements or values of about 0.006 to about 0.020 psi for about 10, 20, 30, 40, 50, 60, 80, 100 seconds or more, preferably about 0.008 to about 0.010 psi for about 10, 20, 30, 40, 50, 60, 80, 100 seconds or more, and preferably for about 0.010 psi for about 10, 20, 30, 40, 50, 60, 80, 100 second or more.

In one embodiment, quality testing of implantable devices 200 in their respective case 1 protects the integrity of the device during quality control testing, reduces the number of manipulations or touches of the implantable device because it remains in the case 1 during quality control testing, sterilization, filling into the device fill pouch assembly as described in detail below, and filling of the implantable device 200 with therapeutic agents, e.g. pancreatic progenitor cells, PDX1-positive pancreatic endoderm cells, endocrine cells, and immature beta cells and the like.

The embodiments herein describe tools and instruments for use with or along with an implantable device having a therapeutic agent therein. Applicants are developing a cell therapy for diabetes, specifically an encapsulated cell therapy to treat diabetes, and have in described in detail various endoderm-lineage or definitive-endoderm lineage cells, specifically pancreatic-lineage cells for use with the embodiments described herein. For example, Applicants have described in detail mesendoderm and definitive endoderm-lineage type cells in at least U.S. application Ser. No. 12/099,759, entitled METHODS OF PRODUCING PANCREATIC HORMONES, filed Apr. 8, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. No. 14/106,330, entitled IN VITRO DIFFERENTIATION OF PLURIPOTENT STEM CELLS TO PANCREATIC ENDODERM CELLS (PEC) AND IMMATURE BETA CELLS, filed Dec. 12, 2013; Ser. No. 14/201,630, filed Mar. 7, 2014; and PCT/US2014/026529, IN VITRO DIFFERENTIATION OF PLURIPOTENT STEM CELLS TO PANCREATIC ENDODERM CELLS (PEC) AND ENDOCRINE CELLS, filed Mar. 13, 2014. In one preferred embodiment, the implantable device consists of a therapeutic agent, a living cell, an endoderm-lineage cell, a definitive endoderm-lineage cell, a progenitor cell, a progenitor cell differentiated from stem cells (or a human embryonic stem cells including those derived from methods now known or to be discovered in the future, fetal stem cells, cord blood stem cell, induced pluripotent stem cells, reprogrammed cells, parthenote cells, gonadal germ cells, and mesenchymal, or hematopoietic stem cells, a pancreatic progenitor cell), a PDX-1 positive pancreatic progenitor cell, an endocrine precursor cell, an endocrine cell, an immature beta cell, an immature islet cell, Device Fill Pouch Assembly (DFPA)

Figure 6:
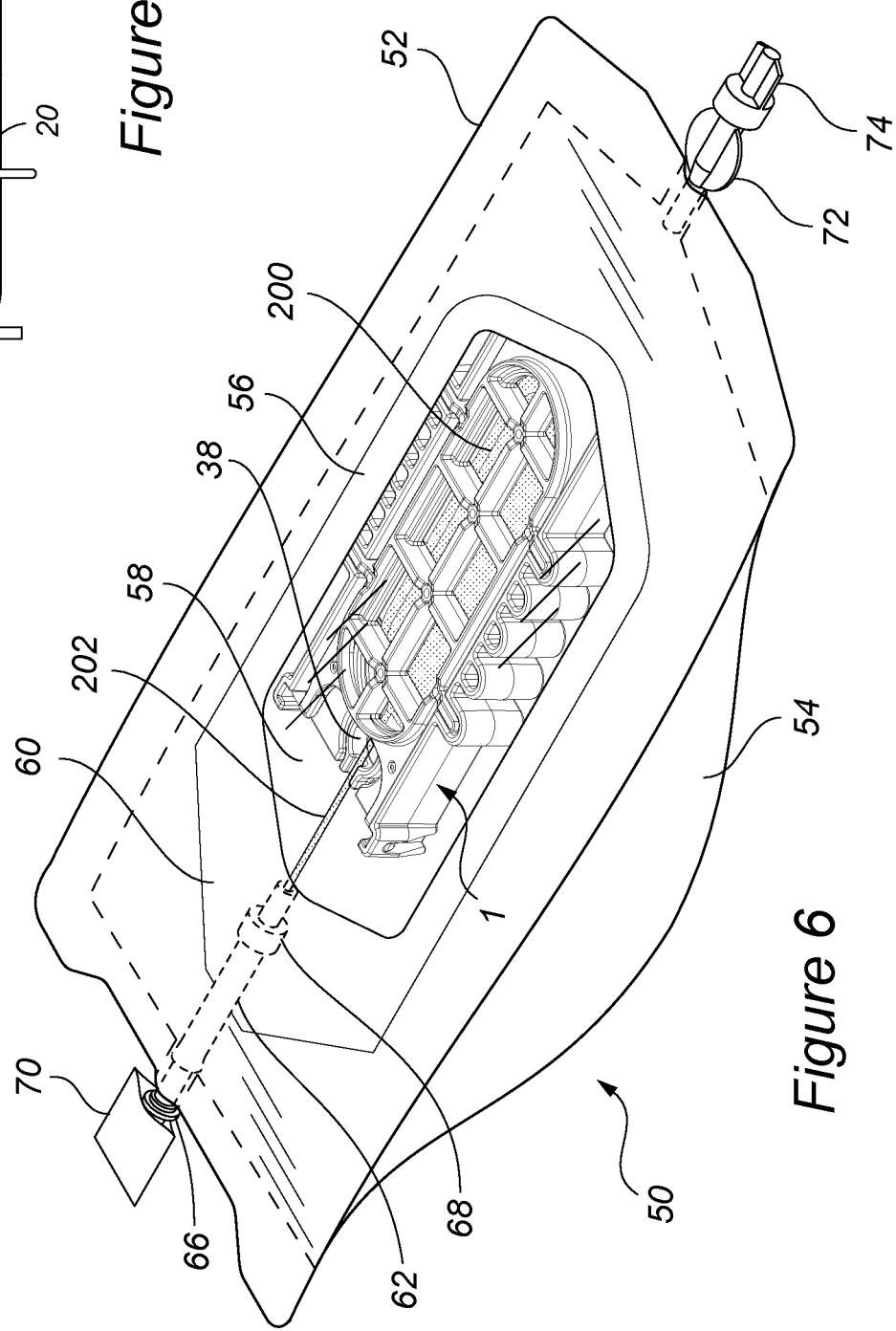
FIG. 6 illustrates a perspective view of a device fill pouch assembly (DFPA) for housing and sterilizing the device case and an implantable device therein according to an embodiment of the invention.

FIG. 6 illustrates a nonlimiting, nonexclusive embodiment of a device fill pouch assembly (DFPA) 50 that functions both as a sterilization bag for the sterilization of the case 1 and implantable device 200 therein, and an assembly to facilitate filling of the implantable device, e.g. cell filling of the implantable device.

As illustrated in FIG. 6, the DFPA 50 is an assembly or system consisting of double peel pouch formed by peelably adhering a first sheet 52 and a second sheet 54, the first sheet 52 having a clear, peelable transparent window 58 for viewing the implantable device 200 and case 1 therein and an inlet and outlet system. The transparent window 58 consists of frangible (pull-away) seals along the periphery 56, 60. The inlet system can consist of a spacer tube 62, which can be permanently affixed and fitted to any fluidic fitting including but not limited to microbore Luers 66, 68, or detachably attached the any fluidic fitting. In one embodiment, the spacer tube 62 can receive the implantable device port 202 therein hence the port 202 is inserted into the spacer tube 62 there through can be further connected to a cell reservoir, for example, which cell fills the implantable device therein. The outlet system consists of drain port 72 and a drain port cap 74 for draining or depleting or emptying excess media, e.g. excess nutritive media. The most exterior parts of the inlet and outlet system may further comprise a cap 74 e.g., a swabable cap, and one or both systems covered in a shroud or sheath 70. Also, it is understood that these inlet and outlet system can be modified or optimized to fit the purpose of the cell or therapeutic agent intended for loading into the implantable device. In one embodiment, suspension cell aggregates are loaded into the implantable device, and certain microbore features help minimize, reduce and prevent clogging or congestion during the cell filling process. The DFPA is wholly sterilizable or made from a sterilizable material or paper, alone or preferably with the case 1 and implantable device 200 therein. In this instance, the case 1 and implantable device 200 are sterilized at the same time and no further separate assembly of the case and implantable device is necessary post sterilization.

The DFPA 50 also functions as an assembly or system, specifically, a container or reservoir, for filling the implantable device 200 with living cells or other therapeutic agent(s). In the instance of a cell therapy for treatment of diabetes mellitus, the implantable device 200 is filled with living pancreatic progenitor cells, e.g. PDX1-positive pancreatic endoderm cells, or PEC, or endocrine precursor cells, or endocrine cells, or immature beta cells. Methods for filling an implantable device including U.S. Pat. No. 5,964,261 to Baxter International Inc. ("'261 Baxter patent") which describes manually wetting, sterilization, filling via a syringe, and sealing of an implant devices. However, in contrast to the implantable devices described in the '261 Baxter patent, the implantable devices envisaged herein have at least 6-fold the volume capacity as that of the much smaller volume Baxter implantable devices, i.e. 250 versus 4.5 μL, 20 μL and 40 μL; and as such, the instant invention contemplates a scaled manufacturing and processes for wetting, sterilization, filling, and sealing of much larger capacity implantable devices. For example, these other implantable devices need to be pre-wetted or prepared before the cells are loaded by injecting or bathing the implantable device in a liquid mixture adequate to pre-wet it, e.g., sterilized water, saline or about 70% to 100% ethanol into DFPA 50 bag through the inlet system. In one embodiment herein, the interior of the implantable device can be primed or wetted, e.g. with cell culture media (not ethanol) before immediately loading the cell aggregate suspension into the implantable device. The priming solution can in this instance be the same solution (or culture media) as that the cell aggregates are suspended in. This is at least one less step than in previously disclosed methods including the '262 Baxter patent and residual ethanol is not a concern. The solution (cell culture media, other nutritive media or other liquid mixture) is drained out of the bag through the outlet system taking steps to remove any air from the implantable device. If water or ethanol is used to pre-wet the implantable device, then saline or cell culture media can be used to flush any residual water or ethanol from the device. If pre-wetting the implantable device is required for cell loading, care must be used to make sure that air bubbles do not get trapped in the fluidic path (e.g. the inlet or outlet systems), which may interference with cell loading. The volumes of cell suspension and media amounts drawn up into the syringe will depend on the maximal volume capacity or size of the implantable device. If desired, less dense cell concentrations may be used. For example, 1×10⁷ cells in a final volume of 30 μL may be used for the 20 μL implantable device. The pre-wetting and filling methods described in the '261 Baxter patent consist of many parts and intended for research and not clinical use, and therefore difficult to maintain a sterile and/or aseptic environment necessary for regulatory compliance for any cell product. Because the DFPA 50 can have a dual function (sterilization and filling assembly), it reduces the likelihood that the implantable device inside the case will be compromised, breached or contaminated. Further, because the '261 Baxter patent devices are significantly smaller in size and volume capacity than the devices in the embodiments herein, cell loading by way of a syringe is feasible although not practical for scale up purposes.

Since sterilization may be conventionally performed with radiation (e.g. ionizing radiation, gamma irradiation, electron beam irradiation), dry heat exposure or high-temperature moisture (e.g., steam (wet heat) exposure, chemical (e.g. ethylene oxide exposure and the like), materials used for the DFPA 50 of the present invention are of a material that allows the effective elements (gases) and water vapor to pass through while not allowing germs or liquid water to pass through. A sterilization systems that is capable of simultaneously sterilizing the DFPA 50, the case 1 and the implantable device 200 is preferred, however, certain case 1 or implantable device 200 materials may not be compatible with high temperatures nor irradiation, and ethylene oxide exposure is a reasonable sterilization approach. Also, sterilization approaches may also dictate choice of sterilization package materials. The packaging materials described herein are compatible with most sterilization methods contemplated above.

The DFPA 50, in particular the sheets 52, 54 of the illustrated embodiment, is formed by peelably adhering base materials or sterilization paper, preferably made of polyester, polyvinyl chloride, polyethylene, polypropylene, ethylene copolymers, ionomer resins or material such as a gas-permeable polyethylene or polypropylene non-woven fabric, strong, lightweight, flexible, resistant to water, chemicals and abrasion. Alternatively, a thermoplastic transparent resin film that exhibits a proper degree of adhesive strength and that serves as a seal layer between the first sheet 52 and second sheet 54 can be laminated between the sheets without harming the gas permeability of the sheets, and the both materials can be sealed and adhered to each other. In other embodiments, the DFPA 50 consists essentially of the same properties as that described in detail for the shipping bag 110 in figure FIG. 11 below.

The transparent window 58 is preferably made of a biaxially-oriented polyethylene terephthalate (trade name is Mylar) or polyester film made from stretched polyethylene terephthalate (PET) and is used for its high tensile strength, chemical and dimensional stability, transparency, reflectivity, and gas and aroma barrier properties. However, other materials with substantially similar properties as that indicated above for each of the base materials for the DFPA 50 or the transparent window 58 are envisaged by the present invention, including any clear polymer film which maintains a sterile barrier under normal handling would be acceptable (e.g. polyethylene).

Device Case Storage Bag

Figure 9:
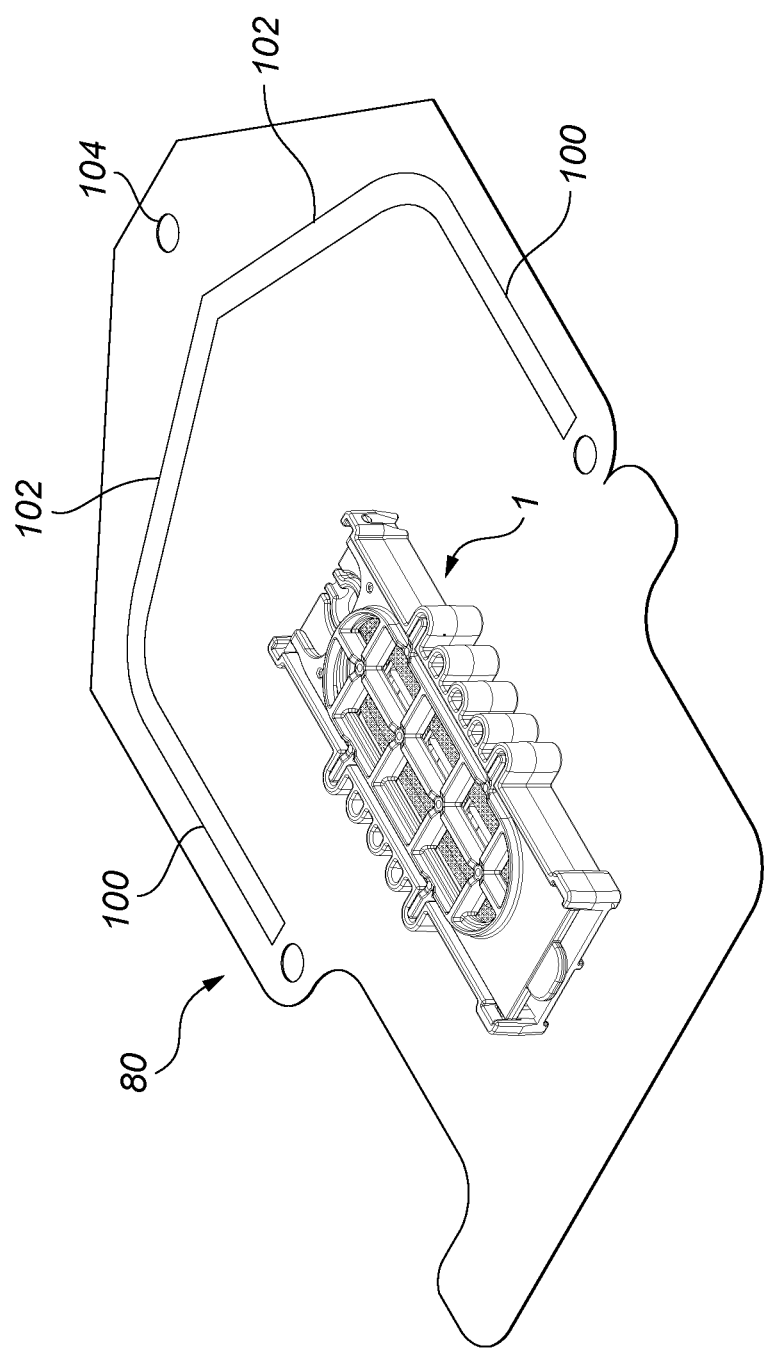
FIG. 9 illustrates a perspective view of a device case storage container with an implantable device case and implantable device therein, with the cover sheet of the container removed for clarity of illustration, according to an embodiment of the invention.

FIGS. 7-9 illustrate a nonlimiting, nonexclusive embodiment of a container or storage bag 80 useful for storing an implantable device 200 filled with cells. FIG. 9 is one perspective view of a bag 80 made in accordance with this invention. The storage bag 80 may be made of conventional construction, including a pair of plastic sheets sealed at periphery 168 and side and upper frangible seals 100, a hanger provision 104 for maintaining the storage bag 80 in an upright position if necessary and various registration holes 84. Alternatively, as illustrated in FIGS. 7-8, the storage bag 80 may also include access ports 86, 92 permanently (e.g., UV bonding) or detachably connected to fluidic fittings 88, 94, 96 and caps 98, 90.

In accordance with this invention, the storage bag 80 is made from a transparent, flexible, sterilizable flexible and strong plastic including but not limited to polyethylene and Ethylene-Vinyl-Acetate (EVA), polyolefins, polyolefin mixtures, polycarbonate, polysulfone, polystyrene, polyvinyl chloride (PVC) plasticized with plasticizers known in the art as di-2-ethylhexyl phthalate (DEHP or DOP) or, in some cases certain triesters of trimellitic acid such as tri-2-ethylhexyl trimellitate (TOTM or TEHTM); and preferably polyethylene and EVA. The material selected for the storage bag 80 is a co-extrusion of polyethylene and EVA, which is advantageous over standard PVC materials because it reduces or prevents plastics leaching into the lumen of the storage bag 80 where the cells are encapsulated, and it reduces general environmental mercury levels typically used in traditional PVC manufacturing. These films and the above PVC plasticizers are described more fully, for example, in U.S. Pat. No. 4,280,497 to W. Warner et al. and U.S. Pat. No. 4,222,379 to D. Smith. However, similar plasticized bags have been found to yield a detectable amount of the ester type plasticizer into the plasma of the blood as it is stored in the bag for a period of days. Accordingly, one embodiment of a storage bag of the invention does not preferably leach plasticizer into the interior of the storage bag, which holds and stores a living cells encapsulated inside an implantable device 200 and case 1 therein. Moreover, the cells encapsulated in the implantable device require an exchange of gases and nutrients, so any flexible plastic material should preferably be gas permeable or impermeable so as to meet the metabolic requirements of the cells stored therein; particularly for long-term storage, to help keep the cells viable.

FIG. 8 shows alternative components for loading the device case 1 into the storage bag 80 to help maintain an aseptic environment and thereby minimally contacting or touching the case 1 and/or implantable device 200. As shown, there is a first sleeve 134 for protecting the upper or top or proximal portion of the storage bag 80 during subsequent sealing for example, and a second sleeve or guide 136 insertably inside the first sleeve 134 to slide the case 1 and filled implantable device 200 into the storage bag 80. After the case 1 and filled implantable device 200 are placed into the storage bag 80, the bag is filled with a cell culture storage medium including but not limited to base mediums such as Dulbecco's Modified Eagle's Medium (DMEM), or CMRL media developed by Connaught Medical Research Laboratories (CMRL), StemPro hESC SFM (Life Technologies), or any appropriate storage medium such that the medium bathes and covers completely and keeps wet the implantable device 200 therein. Once the storage bag 80 is filled, the upper opening is then sealed and can be continuous with the side frangible seal 100 to form a complete seal of the device case, implantable device and storage medium therein. Storage of the filled implantable device 200 in such a manner is suitable for up to 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 25 days and 30 days or more at an appropriate storage temperature to maintain viability of the living cells before transplant.

In one embodiment, the storage bag 80 is formed by creating a wholly peripheral seal 168 and a frangible seal 100, then cutting out the bag such that bottom and side sections of the periphery seal 168 are retained, while the top side and top sections of the periphery seal are not (e.g. these sections are cut out or left off); but the frangible seals 100 remain in-tact. Alternatively, the periphery seal 168 can remain intact alongside the frangible seal 100 depending on the use, e.g. if the use does not require use or peeling away of the frangible seal 100, then the periphery seal 168 can be retained except for the top opening.

The Shipping Bag

FIGS. 10-11 illustrates a non-limiting, nonexclusive shipping bag 110 in accordance with the present invention. The shipping bag 110 is formed from first and second sheets 114, 116 positioned in opposing face-to-face relation and sealed to one another along three sides 112 to form a pouch, leaving an opening 116 along the remaining side suitable for receiving articles, for example, a device case storage bag 80. In the embodiment shown, the sheets 114, 116 are generally square or rectangular in shape and they are sealed to one another along seal areas 112 adjacent opposite side edges of the bag, and along an angularly extending seal area on one side edge of the bag. After the shipping bag 110 has been filled with its contents by the user, it may be sealed aseptically to close the opening keeping the contents inside sterile. Sealing of the sheets 114, 116 to one another may be carried out using conventional heat or ultrasonic sealing equipment as is well known in the art. To maintain aseptic handling, the shipping bag 110 may further comprise one or more handle(s) 118 attached to the exterior of the bag for use in opening and keeping it opened without touching the interior of the bag while the contents are being filled.

In one embodiment, the shipping bag material of FIG. 11 is substantially similar in properties to the DFPA 50 of FIG. 6. Both consist of a heat sealable transparent thermoplastic polymer film inner layer and forms the laminate between two sheets typically made from a sterilizable material or paper. Preferably, the sheet is a polyolefin material, suitable examples of which include polypropylene, polyethylene, ethylene copolymers such as EAA, EMA, EVA and ionomer resins such as Surlyn from DuPont or Iotek from Exxon-Mobil. The laminate and sheets may suitably have a thickness of from about 0.5 mils to about 4.0 mils, more preferably about 1.5 to about 3.0 mils, and most preferably about 2 mils. Alternatively, as illustrated in FIG. 6 for the DFPA 50, the sheets 114, 116 may consist of a transparent material capable of imparting strength, puncture resistance, dimensional stability and durability to the bag. Suitable materials for the transparent material include polyethylene terephthalate (PET), nylon, polypropylene, polyethylene and cellophane. Particularly preferred are biaxially oriented films such as biaxially oriented PET and biaxially oriented nylon. The sheets may have a thickness of from about 0.36 to 2.0 mils, more preferably from about 0.48 to 1.0 mils, and most preferably about 0.48 mils (48 ga). The sheets 114, 116, transparent or not, may additionally have a moisture barrier, for example, a molecularly oriented polychlorotrifluoroethylene (PCTFE) fluoropolymer film. The PCTFE film is transparent, biochemically inert, chemical resistant and free from plasticizers and stabilizers. Preferably the molecularly oriented PCTFE film is a monoaxially oriented film. PCTFE fluoropolymer films are sold by Honeywell, Inc. under the Aclar registered trademark.

Conventional lamination and sealing methods include but are not limited to using a spray adhesive, roll coating, knife over roll coating, wire rod coating, or gravure coating. Suitable adhesives include solvent based, water based or solventless adhesives including acrylic adhesives, epoxy cured polyester urethanes, moisture cured polyester urethanes and isocyanate terminated polyester adhesives. Alternatively, the inner (or middle) laminate layer can be formed directly on the sheets 114, 116 by extrusion coating; and if there is the transparent outer layer, it can be laminated directly to the sheets 114, 116 using known adhesives and techniques as described above. If desired, the inner surface of the transparent layer may be reverse printed prior to laminating to provide a layer of printing with product label or graphics or other information. The sheets 114, 116 may also be surface printed prior to or post lamination.

The Sizer

Figure 12A:
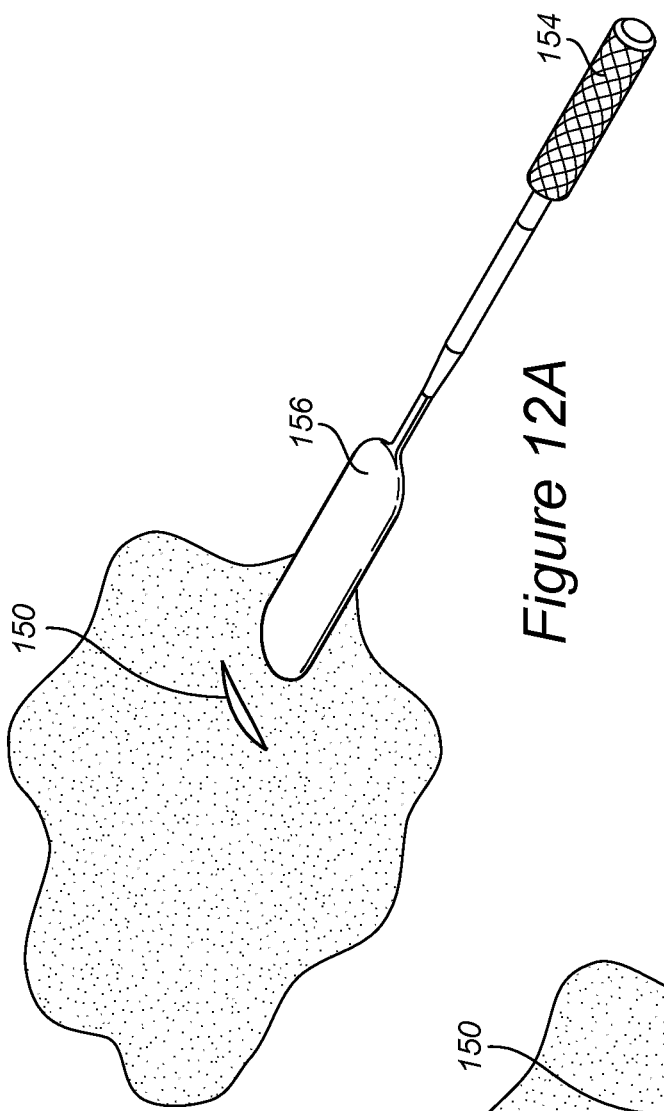
FIGS. 12A-12B illustrate perspective views of a surgical sizer, outside and inside the implant site according to an embodiment of the invention.
Figure 12B:
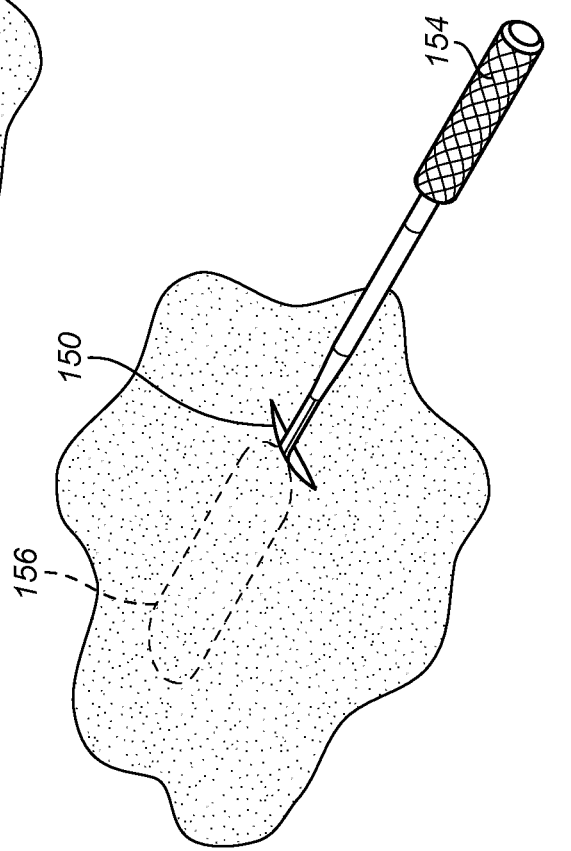

FIG. 12 illustrates a nonlimiting, nonexclusive surgical sizer in accordance with the invention. The sizer 150 includes a distal or pocket-forming portion 156 and proximal or handle portion 154. In the example shown, the pocket-forming portion 156 is approximately the shape, or is approximately the shape that sizes the cavity, of the implantable device 200 to be implanted. Certain detailed aspects of the actual implantable device, such as its port and surface details need not be reproduced in the pocket-forming portion 156; and in fact, omitting such details may serve to simplify manufacturing as well as reduce the number of features that could potentially damage the tissue if not properly fabricated and create a cavity that allows implantable device 200 to conform to the target implant site, regardless of overall geometry. For example, in one embodiment, the sizer is slightly tapered with a sharper leading edge useful to expand out the tissue at the implant site. In one embodiment the pocket-forming portion 156 can have non-planar geometries, for example, the precise shape and curvature of the pocket-forming portion 156 may be bent or tailored to the particular surgical procedure, anatomical site, and access route. Further, the pocket-forming portion 156 may be slightly larger than the actual dimension of the implantable device, for example, it may be scaled to 105%, 110%, 115%, 120%, 125% or 130% or more of the dimension of the implantable device. The pocket-forming portion 156, like the implantable device 200 it replicates, may be shaped to follow the contours of the relevant anatomical implant site so as to prevent causing damage to delicate tissue, for example contoured to the curvature of the back, arm, abdomen, flank, leg, etc.

The proximal or handle portion 154 is an elongated substantially planar handle portion with a grippable handle 154. The handle 154 may be etched, engraved or textured, contain a cut-out (or groove) that is anatomically compatible with a human thumb or index and middle finger to provide the surgeon with an appropriate gripping surface. The cut-out may take the form of a circular hole, an elongated slot, or other shape (e.g., a hook-shape), and have a textured grip for additional feedback. Alternatively, the entire proximal or handle portion including the elongated shaft and the grippable handle 156 can be textured, while keeping the distal or pocket-forming portion 154 relatively smooth. In still another embodiment, the pocket-forming portion 156 may be permanently or detachably coupled to the proximal or handle portion 154.

Still, the sizer 150 can have non-planar geometries, for example, the precise shape and curvature of the proximal or handle portion may be bent or tailored to the particular surgical procedure, anatomical site, and access route. For example, the handle portion may have different sections with different radii of curvature (including planar sections and curved sections). So, depending on the particular application, a sizer 150 in accordance herewith may include differently curved ergonomic handle portion to aid the surgeon in placing the implantable device into the applicable anatomic region, e.g., a particular layer of the dermis, or between the muscle and the dermis.

Also, the sizer 150 may have various markings to assist with use. For example, the pocket-sizing portion 156 may contain markings, which may correspond to the location of anchoring features, or other relevant structural features of the implantable device, or may act like a ruler to measure an implant site, e.g., the pocket-sizing portion 156 has a mark to indicate the placement of anchoring sutures corresponding to suture rings (204 in FIG. 13) in one embodiment of the implantable device 200. The proximal or handle portion may also have markings on the elongated shaft and/or handle, which may aid the surgeon in realizing when the pocket-sizing portion should not be pushed any farther in the posterior direction for example.

Also the sizer may comprise a marking tool such as a felt-tip marker, cauterizing tool, or other comparable marking tool to identify certain locations proximate the anatomic location where an implant should be placed.

Alternatively, the distance markings on the distal and proximal portions may have associated holes or slots that allow the distance to be marked on the tissue using any one of the methods mentioned above. In one embodiment, the pocket-sizing portion 156 may include a hole marking, which allows a pen or cauterizing tool, for example, to mark the desired placement of the implantable device, or to mark the boundaries of the implantable device, or to mark the placement of any sutures. Optionally, additional depth markings at specific distances (e.g., in millimeter increments indicative of the distance to the far edge of the pocket-forming portion) along the handle portion may provide a guide to let the surgeon know when the implantable device has reached its optimum or required depth. The markings may, generally, be tactile and/or visual in nature; for example, they may be grooves or notches perceptible by touch, or simply lines drawn onto the handle portion. Of course, the types and locations of markings described herein are exemplary only and those of skill in the art will readily be able to adapt the markings to surgical tools for a variety of other applications.

In some embodiments, sizing and marking functionalities are not integrated into the same instrument, but instead are provided by two separate surgical instruments.

Materials for manufacturing of such a sizer and/or marking tool are described in detail below.

The Deployer Device

Figure 13H:
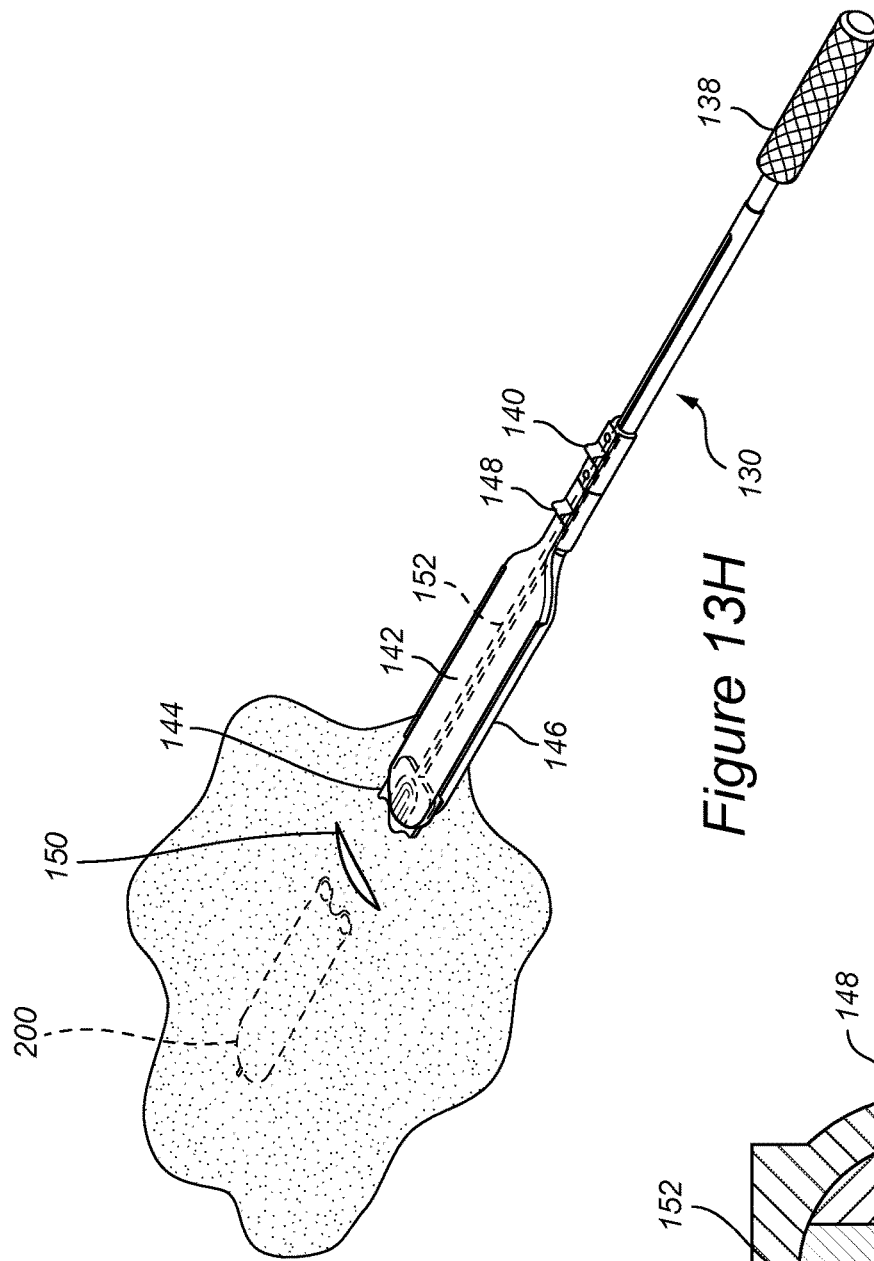

FIG. 13 illustrates a nonlimiting, nonexclusive embodiment of a deployment device ("deployer", or also referred to as a deployer device, deployer tool, deployment tool, delivery tool, delivery device, implantation tool, or implantation device) of the present invention. As used herein a deployer or its equivalent such as "apparatus", "assembly", or "planar assembly" or "system" refer to a tool or instrument capable of retracting, holding, transferring, delivery and deploying a device, such as an implantable device, therein. Generally, the deployer 130 includes at least a proximal and distal end or portions. The distal end also functions as the holder or deployer end 142, 146, 144 and the proximal end also serves as the handle end 138. The total length of the deployer is preferably longer than a length of a deployable implantable device.

The distal end further including at least two holder plates 142, 146, a middle moveable deployer plate or element 144, an elongate shaft 130 the proximal end of which includes a handle 138. The holder plates comprise a cover plate 142 (or cover) and base plate 146 (or base) (or first and second holder, or a first and second plate, respectively), such that the base plate is affixed to a shaft 158 and detachably attached to a handle 138, for example a grippable handle. The base plate 146 may have side walls 174, rails or guides which help placement as well as hold the implantable device in place and prevent the implantable device from slipping. Similarly, the cover plate 142 may have rails or guides 170 which assists in the movements of the cover plate, deployer and base plate relative to each other. When assembled the cover plate 142 and base plate 146 together form a holder for holding the implantable device 200. The distal end further includes a movable deployer plate 144 in between the cover plate 142 and base plate 146 of the holder. The cover plate 142 and deployer plate 144 are assembled and detachably attached or connected to the base plate 146 by way of the base shaft 130 which consists of a rod-shaped shaft 158 with a superior groove along the axis of the shaft 158. The cover plate 142 may also be detachably attached or connected to the base plate 146 by means of a seat, channel, or groove along the inside wall of the base plate 146. The deployer plate 144 is connected or affixed to a deployer shaft 152, which is smaller in diameter than the base holder plate shaft 158, and thereby capable of inserting into the groove or cut out of the base shaft 158 such that it is capable of moving axially along the base shaft 158, or specifically of moving along the top or superior portion of the base shaft 158.

The deployer plate 144 and the cover plate 142 further include control elements 140, 148 on or affixed to the cover plate 142 and the deployer shaft 152, respectively, with the control element 148 (also referred to as the first control element, cover plate control element or cover control element) for the cover plate 142 affixed distal to the deployer control element 140 (also referred to as the second control element, deployer plate control element or deployer control element). The deployer plate 144, the deployer shaft 158 and deployer control element 140 are collectively referred to as the deployer mechanism or deployer apparatus. The deployer plate may also be modified or optimized, e.g. towards the distal end, to accommodate various types of implantable devices. For example, FIG. 13B illustrates an exploded view of the device with a deployer plate, whereby the distal end 160 resembles that of the suture holes or ears 204 of the implantable device.

Figure 13I:
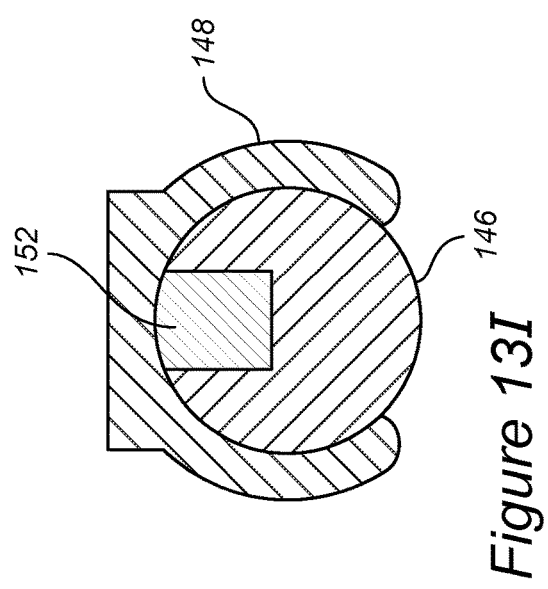

The interconnectedness of these parts is best illustrated in FIG. 13I, which shows how the deployer shaft 152 sits inside the groove of the base shaft 158 and whereby the control elements 140, 148 wrap around both, securing the deployer shaft 152 from leaving the base shaft groove. The cover plate 142 and deployer plate 144, in particular the cover control element 148 and the deployer control element 140 can be threadably moveable inside the base plate 146 rod 158, or ratchetably movable inside the same.

The control elements allow for independent axial movement of the cover plate 142 and deployer plate 144, relative to the base plate 146. The control elements 140, 148 can also be secured by lock tabs, thumb operable wheel, switch or snap or actuator by way of a rounded detent (e.g. a twist), additional force, or additional part and the like, which parts are available and known to one skilled the art. For example, as illustrated in FIGS. 13C-E, to cover and hold the implantable device 200, the user unlatches the latching system (snaps open) the device case 1 and inserts the base plate 146 under the implantable device 200 by pushing (e.g. thumb control) and proximally (or back) the cover plate control element 148. Since, the cover plate control element 148 is affixed distally to the deployer plate control element 140, moving the cover plate control element 148 back towards the handle, or grippable handle 138, also then moves the deployer plate 144 back as well. However, to entirely cover the implantable device 200, the cover plate 142 can be moved distally (forward) to cover the implantable device 200 without while not moving or keeping in place the deployer plate 144 and deployer shaft 152. See, for example, FIG. 13D whereby the two control elements 140, 148 are side by side or directly adjacent to each other, whereas in FIG. 13E they are not side by side but separated, preferably separated by approximately the same distance as length of the cover plate 142 and base plate 146 as well as the implantable device 200.

The deployer 130 as illustrated herein is described for use with the described implantable device 200, other planar and non-planar (e.g. 3-dimensional) implantable devices including semi-permeable planar and non-planar implantable devices are contemplated including but not limited to self-expanding implantable devices, large capacity planar and non-planar or 3-dimensional macro-encapsulation implantable devices. Other encapsulation implantable devices have been described by Applicant, for example, PCT/US2014/022109, 3-DIMENSIONAL LARGE CAPACITY CELL ENCAPSULATION DEVICE, filed Mar. 7, 2014; and U.S. Design application No. 29/408,366 filed Dec. 12, 2011; Ser. No. 29/408,368 filed Dec. 12, 2011; Ser. No. 29/423,365 filed May 31, 2012; Ser. No. 29/447,944 filed Mar. 13, 2013; Ser. Nos. 29/484,363, 29/484,359, 29/484,360, 29/484,357; 29/484,356, 29/484,355, 29/484,362 and 29/484,35, titled 3-DIMENSIONAL LARGE CAPACITY CELL ENCAPSULATION DEVICE and filed Mar. 7, 2014.

Once the implant site is prepared for implantation of the implantable device 200, by way of the sizer 156 as described above, FIGS. 13-F-H illustrate how the implantable device 200 is deployed (also referred to as a deployable implantable device). To deploy the implantable device 200, the user with one hand pushes the deployer control element 140 distally (or forward) while with the other hand, at the same time, move the entire deployer 130 proximally (or backward), thereby deploying the implantable device 200 into the prepared implant site. The implant site can then be closed at the opening site 150. Alternatively, the deployer plate 144 is held in place and the cover plate 142 and base plate 146 are pulled or moving away from the implantable device 200 and implantable site.

Although not illustrated, in one embodiment, the deployer device 130 may further include a grasping system at or near the distal or holder end, or as part of or attached to the deployer plate 144. Such a grasping system is capable of detachably attaching to the implantable device 200 so that when the deployer plate 144 is retracted (moves proximally or backward), the implantable device 200 moves accordingly onto the base plate 146. The grasping system may be controlled, however, from the proximal end of the deployer 130, e.g. with a further control element or actuator similar to that shown for the other two control elements 140, 148 or just by the deployer control element 140. In this instance, such a grasping system may grasp the implantable device suture holes or rings 204, for example, using some type of hook.

Similar to the sizer 156, the distal or holder or deployer end 142, 146, 144 can have non-planar geometries, for example, the precise shape and curvature of the distal or holder or deployer end 142, 146, 144 may be bent or tailored to the particular surgical procedure, anatomical site, and access route. Likewise, the sizer 156, the deployer handle 138 may have non-planar geometries, for example, the precise shape and curvature of the handling portion may be tailored to the particular surgical procedure, anatomical site, and access route. The handle portion may have different sections with different radii of curvature (including planar sections and curved sections). So, depending on the particular application, a deployer 130 in accordance herewith may include differently curved ergonomic handling portions to aid the surgeon in placing the implantable device into the applicable anatomic region, e.g., a particular layer of the dermis, between the muscle and the dermis or other superficial tissue layers. In one embodiment, the rod or shaft 158 and handle 138 may have depth markings or an associated marking tool.

In the embodiments shown, like the sizer, the distal or holder end takes the approximate shape of the implantable device 200 to be implanted. Certain detailed aspects of the actual implantable device, such as its port and surface details need not be reproduced in the pocket-forming portion 156; and in fact, omitting such details may serve to simplify manufacturing as well as reduce the number of features that could potentially damage the tissue if not properly fabricated. Still certain functional features of the implantable device 200 may be incorporated into the deployer to better retrieve, hold, transfer and deploy the implantable device, for example, the most distal end of the deployer plate 144 may adapt approximately the shape of the proximal end of the implantable device 200. As illustrated in FIG. 13B, the deployer plate 144 has two indentations which were adapted so that it matched the suture registration holes or rings 204 at the proximal end of the implantable device 200 in this instance. Other modifications can be made to accommodate other types of implantable devices. Further, the distal or holder end 142, 146 may be slightly larger than the actual dimension of the implantable device, for example, it may be scaled to 105%, 110%, 115%, 120%, 125% or 130% or more. Similar to the sizer 156, holder portion 142, 146, 144 may be shaped to follow the contours of the relevant anatomical implant site so as to prevent causing damage to delicate tissue, for example contoured to the curvature of the back, arm, abdomen, flank, leg, etc.

Figure 14C:
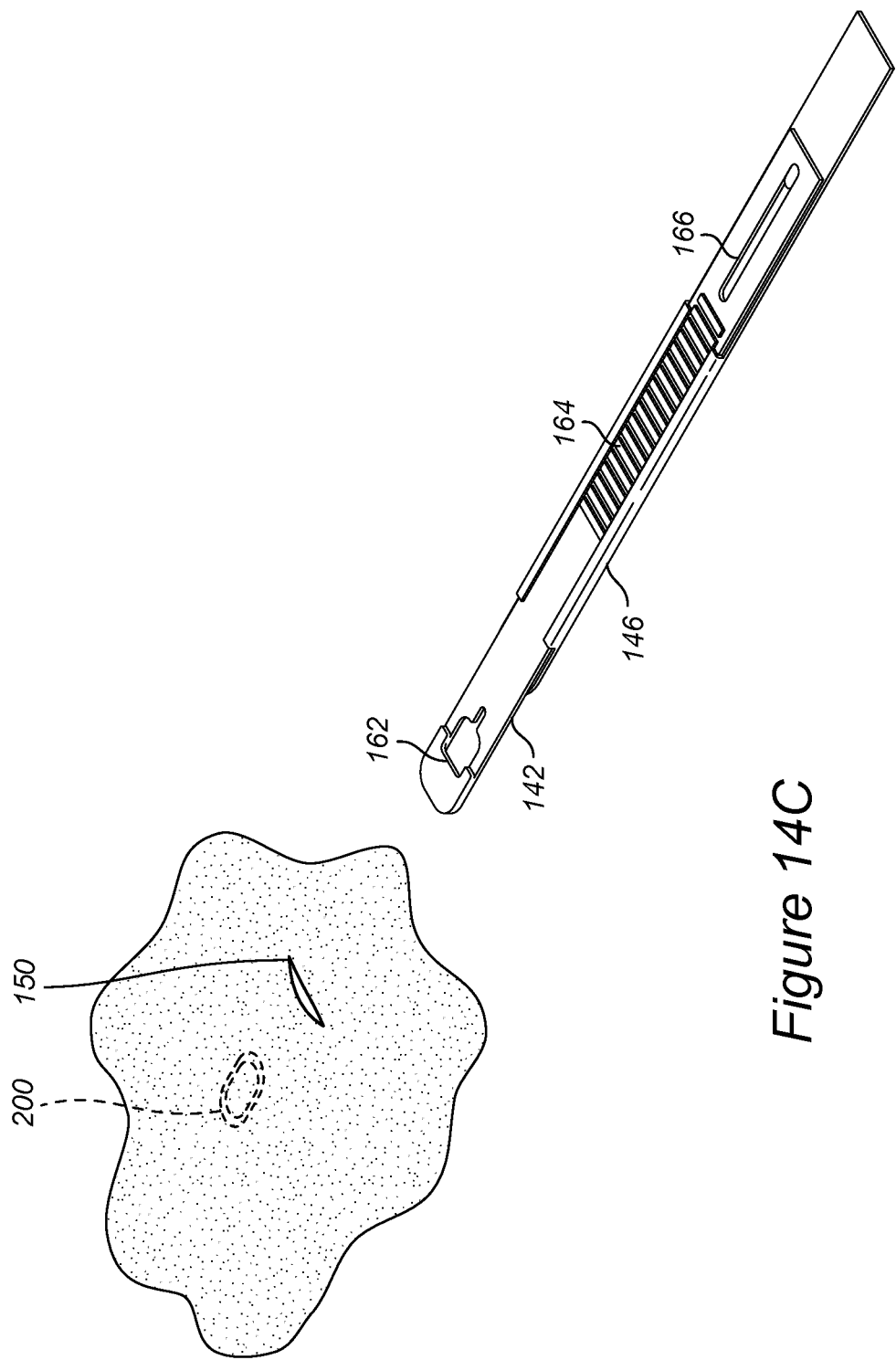

FIGS. 14 A-C illustrate another deployer embodiment of the invention. The deployer generally consists of an interconnected cover plate 142 and base plate 146, without an intermediate deployer plate, operable control elements, or shaft handle as in the above embodiment. The cover plate 142 can alternatively consist of an opening or window 162 to view the implantable device 200. In one embodiment, the attachment system between the cover plate 142 and base plate 146 are detachably attached by a notch on the base plate 146 that inserts into the groove 166 on the cover plate 142. Movement of the two plates 142, 146 relative to each other can be accomplished by a texturing system or gripping system 164 to the cover plate 142, for example, shallow ridges 164 as shown in FIG. 14. Still other embodiments similar to that described previously for the control elements 140, 148 (e.g. thumb operable switch or wheel, lock tabs or snaps by way of a rounded detent) of the deployer 130; and that described for the finger grips 36 (indented grips 120, 122, textured 124, 126, 128, engraved or etched grips 124, and rubberized or textured sticky grips 124, 128) of the device case 1 can be employed or applied to the cover plate 142 herein. Delivering and deploying the implantable device 200 in such an embodiment does not depend on a deployer, rather moving cover plate forward, e.g. by pushing forward (or distally) on the ridges 164.

In one embodiment of the invention, the deployer 130 may be equipped with any a number of holder system at the distal end, since the holder plates will be modified or adapted accordingly to the shape and design of the implantable device, while still keeping the same concept of a slidable system for transferring and deploying the implantable device.

In one embodiment of the invention, the deployer 130 may detachably attach or connect to devices, implantable or not, that are commercially available or currently exist and only nominal modification of the deployer as described here would be required.

In one embodiment of the invention, the control elements can take on other configurations and need not be thumb or finger activated elements as illustrated, for example, it can be a thumb operable wheel or a switch.

In one embodiment of the invention, the control elements may lock at various different positions along the length or axis of the deployer, such locking position may be dependent on the implantable device.

Manufacturing of the Device Case, Sizer and/or Deployer

The device case, surgical sizer, marking tool, and deployer as described herein may be constructed using injection molding, machining, stereolithography, or other 3D manufacturing (e.g. 3D printing) procedures known to persons of skill in the art. The construction of these instruments may be adapted to its intended application and use. For example, a sizer, marker, or deployment tool intended for repeated use may be made of an autoclave-compatible material (i.e., a material that withstands the high-pressure, high-temperature steam used in an autoclave to sterilize the tool), such as metal (e.g., stainless steel, gold, platinum, titanium, niobium, nickel, nickel titanium, cobalt-chrome alloys, molybdenum or molybdenum alloys, or an alloy such as nitonol (a titanium-nickel alloy) or alumina ceramic of comparable properties), or certain biocompatible polymer materials (e.g., polycarbonate, acrylonitrile butadiene styrene (ABS), high-density polyethylene (HDPE), polystyrene, polyether ether ketone (PEEK), polypropylene, urethane, teflon, polyethylene, polymethylmethacrylate, certain epoxies, silicone, or parylene and other polyesters as described above). On the other hand, an instrument intended for one-time use may be manufactured from a disposable polymer material, preferably one that degrades during autoclaving to ensure that the instrument is not used more than once (e.g., caprolactone, lactic acid, glycolic acid, acrylic, polycarbonate, or acrylonitrile butadiene styrene).

The external surfaces of the device case, surgical sizer, marking tool, and deployer are preferably non-abrasive and/or finished with smooth edges in order to prevent damage to the surrounding tissues contacted during implantation. In some embodiments, the instrument is surface-coated with parylene or a comparable hydrophobic material for an optimized smooth surface; surface coatings may be applied to both metal and disposable plastic tools. For example, the instrument may be injected-molded out of polymer (e.g. polycarbonate, ABS, HDPE, polystyrene or polypropylene) and then coated with Parylene C. Additionally, the underside of the instrument may be dipped in silicone or other materials commonly used by those skilled in the field to further optimize the surface. During the coating procedure, the groove, holes, or indentations in the portion of the shaft or handle or the marking portion may be used to hold the instrument so as to minimize the surface area that is not coated with conventional coating procedures.

Various aspects of the invention are described herein, but still others not described in detail but referred to can be found in Applicant's U.S. patent application Ser. No. 10/486,408, entitled METHODS FOR CULTURE OF HESC ON FEEDER CELLS, filed Aug. 6, 2002; Ser. No. 11/021,618, entitled DEFINITIVE ENDODERM, filed Dec. 23, 2004; Ser. No. 11/115,868, entitled PDX1 EXPRESSING ENDODERM, filed Apr. 26, 2005; Ser. No. 11/165,305, entitled METHODS FOR IDENTIFYING FACTORS FOR DIFFERENTIATING DEFINITIVE ENDODERM, filed Jun. 23, 2005; Ser. No. 11/573,662, entitled METHODS FOR INCREASING DEFINITIVE ENDODERM DIFFERENTIATION OF PLURIPOTENT HUMAN EMBRYONIC STEM CELLS WITH PI-3 KINASE INHIBITORS, filed Aug. 15, 2005; Ser. No. 12/729,084 entitled PDX1-EXPRESSING DORSAL AND VENTRAL FOREGUT ENDODERM, filed Oct. 27, 2005; Ser. No. 12/093,590, entitled MARKERS OF DEFINITIVE ENDODERM, filed Nov. 14, 2005; Ser. No. 11/993,399, entitled EMBRYONIC STEM CELL CULTURE COMPOSITIONS AND METHODS OF USE THEREOF, filed Jun. 20, 2006; Ser. No. 11/588,693, entitled PDX1-EXPRESSING DORSAL AND VENTRAL FOREGUT ENDODERM, filed Oct. 27, 2006; Ser. No. 11/681,687, entitled ENDOCRINE PROGENITOR/PRECURSOR CELLS, PANCREATIC HORMONE-EXPRESSING CELLS AND METHODS OF PRODUCTION, filed Mar. 2, 2007; Ser. No. 11/807,223, entitled METHODS FOR CULTURE AND PRODUCTION OF SINGLE CELL POPULATIONS OF HESC, filed May 24, 2007; Ser. No. 11/773,944, entitled METHODS OF PRODUCING PANCREATIC HORMONES, filed Jul. 5, 2007; Ser. No. 11/860,494, entitled METHODS FOR INCREASING DEFINITIVE ENDODERM PRODUCTION, filed Sep. 24, 2007; Ser. No. 12/099,759, entitled METHODS OF PRODUCING PANCREATIC HORMONES, filed Apr. 8, 2008; Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. Nos. 12/765,714 and 13/761,078, both entitled CELL COMPOSITIONS FROM DEDIFFERENTIATED REPROGRAMMED CELLS, filed Apr. 22, 2010 and Feb. 6, 2013; Ser. No. 11/838,054, entitled COMPOSITIONS AND METHODS USEFUL FOR CULTURING DIFFERENTIABLE CELLS, filed Aug. 13, 2007; Ser. No. 12/264,760, entitled STEM CELL AGGREGATE SUSPENSION COMPOSITIONS AND METHODS OF DIFFERENTIATION THEREOF, filed Nov. 4, 2008; Ser. No. 13/259,15, entitled SMALL MOLECULES SUPPORTING PLURIPOTENT CELL GROWTH, filed Apr. 27, 2010; PCT/US11/25628, entitled LOADING SYSTEM FOR AN ENCAPSULATION DEVICE, filed Feb. 21, 2011; Ser. No. 13/992,931, entitled AGENTS AND METHODS FOR INHIBITING PLURIPOTENT STEM CELLS, filed Dec. 28, 2010; and U.S. Design application No. 29/408,366 filed Dec. 12, 2011; and Ser. No. 29/408,368 filed Dec. 12, 2011; Ser. No. 29/423,365 filed May 31, 2012; and Ser. No. 29/447,944 filed Mar. 13, 2013; and U.S. Provisional Application No. 61/774,443, entitled SEMIPERMEABLE MACRO IMPLANTABLE CELLULAR ENCAPSULATION DEVICES, filed Mar. 7, 2013; 61/775,480, entitled CRYOPRESERVATION, HIBERNATION AND ROOM TEMPERATURE STORAGE OF ENCAPSULATED PANCREATIC ENDODERM CELL AGGREGATES, filed Mar. 8, 2013; Ser. No. 14/106,330, entitled IN VITRO DIFFERENTIATION OF PLURIPOTENT STEM CELLS TO PANCREATIC ENDODERM CELLS (PEC) AND ENDOCRINE CELLS, filed Dec. 13, 2013; PCT/US2014/022065, entitled CRYOPRESERVATION, HIBERNATION AND ROOM TEMPERATURE STORAGE OF ENCAPSULATED PANCREATIC ENDODERM CELL, filed Mar. 7, 2014; PCT/US2014/022109, SEMIPERMEABLE MACRO IMPLANTABLE CELLULAR ENCAPSULATION DEVICES, filed Mar. 7, 2014; Ser. No. 14/201,630, filed Mar. 7, 2014; and PCT/US2014/026529, IN VITRO DIFFERENTIATION OF PLURIPOTENT STEM CELLS TO PANCREATIC ENDODERM CELLS (PEC) AND ENDOCRINE CELLS, filed Mar. 13, 2014 the contents of which are incorporated herein by reference in their entirety.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. In particular, embodiments of the invention need not include all of the features nor have all of the advantages described herein. Rather, they may possess any subset or combination of features and advantages. Accordingly, the described embodiments are to be considered in all respects as only illustrative and not restrictive.

EMBODIMENTS

The embodiments disclosed herein include the following.

Device Case

Embodiment 1

A case for holding an implantable planar-shape device, the case comprising: a detachably connected cover body and base body, wherein the cover body has a first latch portion and the base body has a second latch portion configured to secure the cover body to the base body when the case is in a closed position, and wherein the cover body and the base body when secured comprise a volume having at least one opening to allow passage of one or more biologically active materials therethrough.

The case of embodiment 1, wherein the case further comprises an implantable device.

The case of embodiment 1, wherein the implantable device is a semi-permeable macro-encapsulation device.

The case of embodiment 1, wherein the implantable device further comprises therapeutic agents therein.

The case of embodiment 1, wherein the therapeutic agents are living cells.

The case of embodiment 1, wherein the living cells are progenitor cells differentiated from stem cells in vitro.

The case of embodiment 1, wherein the progenitor cells are endoderm-lineage cells.

The case of embodiment 1, wherein the progenitor cells are pancreatic progenitor cells.

The case of embodiment 1, wherein the progenitor cells are PDX1-positive pancreatic endoderm cells.

The case of embodiment 1, wherein the living cells are endocrine cells.

The case of embodiment 1, wherein the living cells are immature beta cells.

The case of embodiment 1, wherein the stem cells are selected from the group consisting of human embryonic stem cells, fetal stem cells, cord blood stem cell, induced pluripotent stem cells, reprogrammed cells, parthenote cells, gonadal germ cells, and mesenchymal, or hematopoietic stem cells.

The case of embodiment 1, wherein the cover body and base body are configured to have at least one or more openings to allow passage of one or more biologically active materials there through.

The case of embodiment 1, wherein the cover body and base body each have two openings;

The case of embodiment 1, wherein the cover body and base body each have four openings.

The case of embodiment 1, wherein the cover body and base body each have six openings.

The case of embodiment 1, wherein the cover body and base body each have eight openings.

The case of embodiment 1, wherein the case further comprises finger grips.

The case of embodiment 1, wherein the case comprises a closing or attachment system.

The case of embodiment 1, wherein the attachment system is selected from the group consisting of a hinge, a latch and a snap.

The case of embodiment 1, wherein the case is sterilizable alone or with an implantable device in the case.

The case of embodiment 1, wherein the case further comprises an implantable device port sealing area.

The case of embodiment 1, wherein the case comprises a biocompatible polymer material or a metal.

The case of embodiment 1, wherein the metal is selected from the group consisting of stainless steel, gold, platinum, titanium, niobium, nickel, nickel titanium, cobalt-chrome alloys, molybdenum or molybdenum alloys, or an alloy such as nitonol or alumina ceramic.

The case of embodiment 1, wherein the biocompatible polymer material is selected from the group consisting of, polycarbonate, acrylonitrile butadiene styrene (ABS), high-density polyethylene (HDPE), polystyrene, polyether ether ketone (PEEK), polypropylene, urethane, teflon, polyethylene, polymethylmethacrylate, epoxy, silicone, or parylene.

The case of embodiment 1, wherein biocompatible polymer material or a metal is autoclave-safe.

The case of embodiment 1, wherein the case is a polycarbonate.

The case of embodiment 1, further comprising a finger grip and a port sealing area.

Embodiment 2

A case comprising: a cover body and a base body configured to be secured to each other in a closed condition and configured to define an enclosure in the closed condition such that an implantable device may be located between the cover body and base body, and wherein the cover body and base body each have at least one window to allow passage of one or more biologically active materials there through.

Embodiment 3

A method for quality control testing an implantable device, the method comprising: performing at least one quality control test on an implantable device that is located within a device case; measuring at least one testing parameter using at least one quality index value; and determining quality of the implantable device from said at least one quality index value.

The method of embodiment 3, wherein the quality control test is a dry visual inspection, a wet visual inspection and a pressure decay test.

The method of embodiment 3, wherein the quality control test is a dry visual inspection.

The method of embodiment 3, wherein the quality control test is a wet visual inspection.

The method of embodiment 3, wherein the quality control test is a pressure decay test.

The method of embodiment 3, wherein the implantable device is suitable for use when pressure decay value is about 0.008 to about 0.010 psi for at least 20 or more seconds.

The method of embodiment 3, wherein the implantable device is suitable for use when pressure decay value is about 0.008 to about 0.010 psi for at least 20 or more seconds.

The method of embodiment 3, wherein the implantable device is suitable for use when pressure decay value is about 0.008 to about 0.010 psi for at least 30 or more seconds.

The method of embodiment 3, wherein the implantable device is suitable for use when pressure decay value is about 0.008 to about 0.010 psi for at least 40 or more seconds.

The method of embodiment 3, wherein the implantable device is suitable for use when pressure decay value is about 0.008 to about 0.010 psi for at least 50 or more seconds.

The method of embodiment 3, wherein the implantable device is suitable for use when pressure decay value is about 0.008 to about 0.010 psi for at least 60 or more seconds.

The method of embodiment 3, wherein the implantable device is suitable for use when pressure decay value is about 0.008 to about 0.010 psi for at least 80 or more seconds.

The method of embodiment 3, wherein the implantable device is suitable for use when pressure decay value is about 0.008 to about 0.010 psi for at least 100 or more seconds.

Device Fill Pouch Assembly

Embodiment 4

An assembly comprising: a pouch holding an implantable device with at least one port wherein the pouch comprises an inlet and outlet system, wherein the inlet system extends interiorly into the pouch and is detachably connected to the implantable device port and is detachably connected to a cell reservoir, and wherein the outlet system extends outside of the pouch.

The assembly of embodiment 4, wherein the pouch further comprises a peelable first and second sheet.

The assembly of embodiment 4, wherein the peelable first sheet of the pouch further comprises a peelable transparent window.

The assembly of embodiment 4, wherein the assembly is comprised of a sterilizable material.

The assembly of embodiment 4, wherein the sterilizable material comprises a polyolefin.

The assembly of embodiment 4, wherein the polyolefin is selected from a group consisting of polypropylene, polyethylene, ethylene copolymers and ionomer resins.

The assembly of embodiment 4, wherein the pouch is comprised of a sterilizable material.

The assembly of embodiment 4, wherein the pouch is sterilized by heat, chemical and/or radiation sterilization.

The assembly of embodiment 4, wherein the pouch is sterilized by steam sterilization.

The assembly of embodiment 4, wherein the pouch is sterilized by ethylene oxide.

The assembly of embodiment 4, wherein the pouch is sterilized by ionizing radiation sterilization.

Embodiment 5

A method of filling an implantable device with living cells inside a pouch, the method comprising: a pouch comprising a peelable first and second sheet and in inlet and outlet systems; an implantable device case comprising a cover body and base body and a port sealing area; and an implantable device between the cover body and base body of the implantable device case comprising at least one port, wherein the port is connected to the inlet system of the pouch and further connected to a cell reservoir, wherein the cell reservoir is capable of delivering living cells into the implantable device, thereby filling the implantable device with cells inside the pouch.

The method of embodiment 5, wherein the pouch, the implantable device case and the implantable device are sterilizable.

The method of embodiment 5, wherein the method is performed under aseptic conditions.

The method of embodiment 5, wherein the pouch comprises a cell nutritive media having one or more biologically active materials.

The method of embodiment 5, wherein the nutritive media is any cell culture media appropriate to maintain the living cells.

The method of embodiment 5, wherein the living cells are pancreatic progenitor cells.

The method of embodiment 5, wherein the living cell is a progenitor cell differentiated from stem cells in vitro.

The method of embodiment 5, wherein the progenitor cells are an endoderm-lineage cells.

The method of embodiment 5, wherein the progenitor cells are pancreatic progenitor cells.

The method of embodiment 5, wherein the pancreatic progenitor cells are PDX1-positive pancreatic endoderm cells.

The method of embodiment 5, wherein the living cells are endocrine cells.

The method of embodiment 5, wherein the living cells are immature beta cells.

The method of embodiment 5, wherein the implantable device is a semi-permeable macro-encapsulation device capable of allowing passage of one or more biologically active materials there through.

The method of embodiment 5, wherein outlet port means is open to deplete excess nutritive media.

The Surgical Sizer

Embodiment 6

A surgical sizer comprising a pocket-forming portion and a handle portion, wherein the pocket-forming portion comprises a leading edge for forming an implant site.

The surgical sizer of embodiment 6, wherein the implant site is for an implantable device.

The surgical sizer of embodiment 6, wherein the pocket-forming portion is greater than 100% of the dimension as the implantable device.

The surgical sizer of embodiment 6, wherein the pocket-forming portion is about 105% of the dimension as the implantable device.

The surgical sizer of embodiment 6, wherein the pocket-forming portion is about 110% of the dimension as the implantable device.

The surgical sizer of embodiment 6, wherein the pocket-forming portion is about 120% of the dimension as the implantable device.

The surgical sizer of embodiment 6, wherein the pocket-forming portion is about 125% of the dimension as the implantable device.

The surgical sizer of embodiment 6, wherein the pocket-forming portion is about 130% of the dimension as the implantable device.

The surgical sizer of embodiment 6, comprising of a biocompatible polymer material or a metal.

The surgical sizer of embodiment 6, wherein the metal is selected from the group consisting of stainless steel, gold, platinum, titanium, niobium, nickel, nickel titanium, cobalt-chrome alloys, molybdenum or molybdenum alloys, or an alloy such as nitonol or alumina ceramic.

The surgical sizer of embodiment 6, wherein the polymer material is selected from the group consisting of polycarbonate, acrylonitrile butadiene styrene (ABS), high-density polyethylene (HDPE), polystyrene, polyether ether ketone (PEEK), polypropylene, urethane, teflon, polyethylene, polymethylmethacrylate, epoxy, silicone, or parylene.

The instrument of embodiment 6, wherein the metal consists essentially of stainless steel, titanium, niobium, nickel titanium, or an alloy.

The surgical sizer of embodiment 6, wherein the metal consists essentially of stainless steel.

The surgical sizer of embodiment 6, wherein biocompatible polymer material or a metal is autoclave-safe.

The surgical sizer of embodiment 6, wherein the pocket-forming portion comprises a replica of the implantable device.

The surgical sizer of embodiment 6, wherein a surface of the pocket-forming portion has a curvature that is complementary to an internal anatomical contour.

The surgical sizer of embodiment 6, wherein the pocket-portion is planar.

The surgical sizer of embodiment 6, wherein the pocket-portion is non-planar.

The instrument of embodiment 6, wherein the handle portion is planar.

The surgical sizer of embodiment 6, wherein the handle portion is non-planar.

The surgical sizer of embodiment 6, wherein the handle portion comprises depth markings.

The surgical sizer of embodiment 6, further comprising a marking tool configured to mark tissue.

The surgical sizer of embodiment 6, wherein the instrument is one piece.

The surgical sizer of embodiment 6, wherein the instrument comprises the pocket-forming and handle portion are detachably connected.

Deployer

Embodiment 7

An apparatus for holding and deploying an implantable device, the apparatus comprising a proximal end and a distal end, wherein the distal end comprises a holder comprising a cover plate and base plate for holding the device, and a movable deployer plate for deploying the implantable device from the distal end.

The apparatus of embodiment 7, wherein the cover plate and base plate house the implantable device.

The apparatus of embodiment 7, wherein the base plate further comprises a shaft and a handle, and wherein the shaft is detachably connected to the cover plate and deployer plate.

The apparatus of embodiment 7, wherein the cover plate and deployer plate comprise control elements capable of moving the cover plate and deployer plate axially along the shaft.

The apparatus of embodiment 7, wherein the shaft and handle comprise depth markings.

The apparatus of embodiment 7, wherein the implantable device is deployed by axially moving the deployer plate distally relative to the base plate and cover plate, thereby deploying the implantable device.

The apparatus of embodiment 7, wherein the control elements are a thumb operable wheel or switch.

The apparatus of embodiment 7, wherein the first and second control element is an actuator.

The apparatus of embodiment 7, wherein the implantable device is a planar device.

The apparatus of embodiment 7, wherein the implantable device is a self-expanding device.

The apparatus of embodiment 7, wherein the implantable device is a semi-permeable macro-encapsulation device.

The apparatus of embodiment 7, wherein the implantable device comprises therapeutic agents therein.

The apparatus of embodiment 7, wherein the therapeutic agents are living cells.

The apparatus of embodiment 7, wherein the living cells are progenitor cells differentiated from stem cells in vitro.

The apparatus of embodiment 7, wherein the stem cells are selected from the group consisting of human embryonic stem cells, fetal stem cells, cord blood stem cell, induced pluripotent stem cells, reprogrammed cells, parthenote cells, gonadal germ cells, and mesenchymal, or hematopoietic stem cells.

The apparatus of embodiment 7, wherein the progenitor cells are endoderm-lineage cells.

The apparatus of embodiment 7, wherein the progenitor cells are pancreatic progenitor cells.

The apparatus of embodiment 7, wherein the progenitor cells are PDX1-positive pancreatic endoderm cells.

The apparatus of embodiment 7, wherein the progenitor cells are endocrine cells.

The apparatus of embodiment 7, wherein the living cells are immature beta cells.

Embodiment 8

An assembly for deploying an implantable device comprising: a first holder; a second holder comprising a rod or shaft and a handle; and a deployer mechanism between said first and second holder, wherein the deployer mechanism is adapted to effect deployment of an implantable device, wherein the first holder and deployer mechanism are detachably connected to the second holder rod and is capable of movement along the long axis of the rod; and wherein movement of the deployer mechanism relative to the first and second holder delivers or deploys the implantable device.

The assembly of embodiment 8, wherein the first holder comprises a first control element for axially moving the first holder.

The assembly of embodiment 8, wherein the deployer comprises a distal and proximal end, wherein the distal end is between the first and second holder and the proximal end is interconnected to the rod.

The assembly of embodiment 8, wherein the deployer mechanism further comprises a second control element for axially moving the deployer.

The assembly of embodiment 8, wherein the second control element of the deployer mechanism is threadably movable within the rod.

The assembly of embodiment 8, wherein the second control element of the deployer mechanism is ratchetably movable within the rod.

The assembly of embodiment 8, wherein the first and second control elements are thumb operable wheels or switches.

The assembly of embodiment 8, wherein the first and second control elements are actuators.

The assembly of embodiment 8, wherein the rod and handle of the first holder comprise depth markings.

The assembly of embodiment 8, wherein the implantable device is a planar device.

The assembly of embodiment 8, wherein the implantable device is a self-expanding device.

The assembly of embodiment 8, wherein the implantable device is a semi-permeable macro-encapsulation device.

The assembly of embodiment 8, wherein the implantable device comprises therapeutic agents therein.

The assembly of embodiment 8, wherein the therapeutic agents are living cells.

The assembly of embodiment 8, wherein the living cells are progenitor cells differentiated from stem cells in vitro.

The assembly of embodiment 8, wherein the progenitor cell is an endoderm-lineage cell.

The assembly of embodiment 8, wherein the progenitor cell is a pancreatic progenitor cell.

The assembly of embodiment 8, wherein the progenitor cells are PDX1-positive pancreatic endoderm cells.

The assembly of embodiment 8, wherein the living cells are endocrine cells.

The assembly of embodiment 8, wherein the living cells are immature beta cells.

The assembly of embodiment 8, wherein the metal is selected from the group consisting of stainless steel, gold, platinum, titanium, niobium, nickel, nickel titanium, cobalt-chrome alloys, molybdenum or molybdenum alloys, or an alloy such as nitonol or alumina ceramic.

The assembly of embodiment 8, wherein the polymer material is selected from the group consisting of, polycarbonate, acrylonitrile butadiene styrene (ABS), high-density polyethylene (HDPE), polystyrene, polyether ether ketone (PEEK), polypropylene, urethane, teflon, polyethylene, polymethylmethacrylate, epoxy, silicone, or parylene.

The assembly of embodiment 8, wherein the metal consists essentially of stainless steel, titanium, niobium, nickel titanium, or an alloy.

The assembly of embodiment 8, wherein the metal consists essentially of stainless steel.

Embodiment 9

A method of deploying an implantable device for a cell therapy, the method comprising the steps of: positioning at an anatomical implantation site an implantable device and an assembly comprising a holder having a first and second plate and a deployer plate, wherein the second holder further comprises a rod and handle, wherein the deployer element is connected to the rod and is capable of moving along the axis of the rod; and moving the deployer element relative to rod and first and second holder; thereby deploying or delivering the implantable device at the anatomical implantation site.

The method of embodiment 9, wherein the implantable device is a planar device.

The method of embodiment 9, wherein the implantable device is a self-expanding device.

The method of embodiment 9, wherein the implantable device is a semi-permeable macro-encapsulation device.

The method of embodiment 9, wherein the implantable device comprises therapeutic agents therein.

The method of embodiment 9, wherein the therapeutic agents are living cells.

The method of embodiment 9, wherein the living cells are progenitor cells differentiated from stem cells in vitro.

The method of embodiment 9, wherein the progenitor cells are an endoderm-lineage cells.

The method of embodiment 9, wherein the progenitor cells are pancreatic progenitor cells.

The method of embodiment 9, wherein the progenitor cells are PDX1-positive pancreatic endoderm cells.

The method of embodiment 9, wherein the living cells are endocrine cells.

The method of embodiment 9, wherein the living cells are immature beta cells.

The invention claimed is:

1. A device-fill pouch assembly (DFPA) comprising:
   a pouch, a device case, and an implantable device disposed within the device case, wherein the device case and the implantable device are disposed within the pouch, wherein the pouch comprises:
   a) a first sheet peelably adhered to a second sheet;
   b) a first opening comprising an inlet system for use in loading the implantable device with living cells, wherein the inlet system comprises a spacer tube that extends interiorly into an inner space of the pouch between the first and second sheets;
   c) a second opening comprising an outlet system for use in removing solution from the pouch; and
   d) one or more transparent windows to view the implantable device within the pouch,
   wherein the implantable device comprises an inlet port that extends through the spacer tube.

2. The DFPA of claim 1, wherein the implantable device is a semi-permeable encapsulation device.

3. The DFPA of claim 1, wherein the pouch is made of a sterilizable material or paper.

4. The DFPA of claim 1, wherein the transparent window comprises a biaxially-oriented polyethylene terephthalate, a polyester film comprising stretched polyethylene terephthalate (PET), clear polymer film, or polyethylene.

5. The DFPA of claim 1, wherein the first or second sheet comprises polyester, polyvinyl chloride, polyethylene, polypropylene, polyolefin, an ethylene copolymer, ethylene-vinyl acetate (EVA), ethylene-methyl acrylate (EMA), ethylene-acrylic acid (EAA), an ionomer resin, a gas-permeable polyethylene fabric, a polypropylene non-woven fabric, a water-resistant fabric, a fabric resistant to chemical, or a fabric resistant to abrasion.

6. The DFPA of claim 1,
   a) wherein the first or second sheet comprises a sterilizable paper; or
   b) wherein the first and second sheet have a thickness of 0.5 mils to 4.0 mils, or 1.5 mils to 3.0 mils, or 2 mils.

7. The DFPA of claim 1, further comprising:
a) a thermoplastic transparent resin film that is adhered between the first and second sheet; or
b) a thermoplastic polymer film that is adhered between the first and second sheet.

8. The DFPA of claim 1, wherein the living cells are pancreatic progenitor cells, pancreatic and duodenal homeobox 1 (PDX-1) positive pancreatic endoderm cells, pancreatic endocrine precursor cells, or immature beta cells.

9. The DFPA of claim 1, wherein the outlet system extends outside of the pouch, and wherein the outlet system comprises a drain port that extends through the second opening to the inner space of the pouch.

10. The DFPA of claim 3, wherein the pouch is used to sterilize the implantable device; or the pouch is used to sterilize and fill the implantable device.

11. A device-fill pouch assembly (DFPA) comprising:
a pouch, a device case, and an implantable device disposed within the device case, wherein the device case and the implantable device are disposed within the pouch, wherein the pouch comprises:
a) a first sheet peelably adhered to a second sheet;
b) a first opening comprising an inlet system for use in loading the implantable device with living cells, wherein the inlet system comprises a spacer tube that extends interiorly into an inner space of the pouch between the first and second sheets;
c) a second opening comprising an outlet system for use in removing solution from the pouch; and
d) one or more transparent windows to view the implantable device within the pouch,
wherein the implantable device comprises an inlet port that extends through the spacer tube, wherein the case comprises a base body and a cover body, and wherein the cover body is movable between a closed position where the base body and cover body are coupled to one another and open position where the implantable device can be moved into and out of the case.

12. The DFPA of claim 1, wherein the case comprises a plurality of rigid sidewalls that define a volume for receiving the implantable device therein.

13. A device-fill pouch assembly (DFPA) comprising:
a pouch, a device case, and an implantable device disposed within the device case, wherein the device case and the implantable device are disposed within the pouch, wherein the pouch comprises:
a) a first sheet peelably adhered to a second sheet;
b) a first opening comprising an inlet system for use in loading the implantable device with living cells, wherein the inlet system comprises a spacer tube that extends interiorly into an inner space of the pouch between the first and second sheets;
c) a second opening comprising an outlet system for use in removing solution from the pouch; and
d) one or more transparent windows to view the implantable device within the pouch,
wherein the implantable device comprises an inlet port that extends through the spacer tube, wherein the case comprises a detachably connected cover body and base body, and wherein the cover body has a first attachment portion and the base body has a second attachment portion, the first and second attachment portions configured to secure the cover body to the base body when the case is in a closed position.

* * * * *